United States Patent [19]

Herlyn et al.

[11] Patent Number: 5,633,142
[45] Date of Patent: May 27, 1997

[54] WT1 MONOCLONAL ANTIBODIES AND METHODS OF USE THEREFOR

[75] Inventors: Meenhard Herlyn, Wynnewood, Pa.; Jennifer Morris, Brookfield, Wis.; Frank J. Rauscher, III, Cranbury, N.J.; Ulrich Rodeck, Philadelphia, Pa.

[73] Assignee: The Wistar Institute of Anatomy and Biology, Philadelphia, Pa.

[21] Appl. No.: 456,907

[22] Filed: Jun. 1, 1995

Related U.S. Application Data

[63] Continuation-in-part of Ser. No. 234,783, Apr. 28, 1994.

[51] Int. Cl.$^6$ .................. G01N 33/547; G01N 33/53; C07K 16/30; C07K 16/18
[52] U.S. Cl. .................. 435/7.23; 435/7.1; 435/7.2; 435/7.21; 530/387.1; 530/387.7; 530/388.1; 530/388.8; 530/809
[58] Field of Search ................. 435/7.23, 7.1, 435/7.2, 7.21; 530/387.1, 387.7, 388.1, 388.8, 809

[56] References Cited

U.S. PATENT DOCUMENTS

| | | | |
|---|---|---|---|
| 5,141,736 | 8/1992 | Iwasa et al. | 530/387.3 |
| 5,350,840 | 9/1994 | Call et al. | 536/23.1 |

FOREIGN PATENT DOCUMENTS

| | | |
|---|---|---|
| WO91/07509 | 5/1991 | WIPO |

OTHER PUBLICATIONS

F. Rauscher et al, "Binding of the Wilms' Tumor Locus Zinc Finger Protein to the EGR-1 Consensus Sequence", *Science*, 250:1259-1262 (Nov. 30, 1990).
Z. Wang et al, "The Wilms' Tumor Gene Product, WT1, Represses Transcription of the Platelet-derived Growth Factor A-chain Gene", *J. Biol. Chem.*, 267(31):21999-22002 (Nov. 5, 1992) [Wang I].
Z. Wang et al, "The Wilms' Tumor Gene Product WT1 Activates or Suppresses Transcription Through Separate Functional Domains", *J. Biol. Chem.*, 268(13):9172-9175 (May 5, 1993) [Wang II].
I. Drummond et al, "Repression of the Insulin-Like Growth Factor II Gene by the Wilms Tumor Suppressor WT1", *Science*, 257:674-678 (Jul. 31, 1992).
A. Gashler et al, "Human Platelet-drived Growth Factor A Chain is Transcriptionally Repressed by the Wilms Tumor Suppressor WT1", *Proc. Natl. Acad. Sci., USA*, 89:10984-10988 (Nov., 1992).
S. Madden et al, "Trascriptional Repression Mediate by the WT1 Wilms Tumor Gene Product", *Science*, 253:1550-1553 (Sep. 27, 1991) [Madden I].
S. Madden et al, "A Structure-Function Analysis of Transcriptional Repression Mediated by the WT1, Wilms' Tumor Suppressor Protein", *Oncogene*, 8(7):1713-1720 (Jul., 1993) [Madden II].
S. Maheswaran et al, "Physical and Functional Interaction Between WT1 and p53 Proteins", *Proc. Natl. Acad. Sci. USA*, 90:5100-5104 (Jun., 1993).

W. Bruening et al, "Analysis of the 11p13 Wilms' Tumor Suppressor Gene (WT1) in Ovarian Tumors", *Cancer Invest.*, 11(4):393-399 (Jul., 1993).
H. Miwa et al, "Expression of the Wilms' Tumor Gene (WT1) in Human Leukemias", *Leukemia*, 6(5):405-409 (May, 1992).
T. Miyagi et al, "Expression of the Candidate Wilms' Tumor Gene, WT1, in Human Leukemia Cells", *Leukemia*, 7(7):970-977 (Jul., 1993).
D. Haber et al, "An Internal Deletion with an 11p13 Zinc Finger Gene Contributes to the Development of Wilms' Tumor", *Cell*, 61:1257-1269 (Jun. 29, 1990).
K. Pritchard-Jones et al, "The Candidate Wilms' Tumour Gene is Involved in Genitourinary Development", *Nature*, 346:194-197 (Jul. 12, 1990).
S. Park et al, "The Wilms Tumour Gene WT1 is Expressed in Murine Mesoderm-Derived Tissues and Mutated in a Human Mesothelioma", *Nat. Genet.*, 4:415-420 (Aug., 1993).
R. Pisani et al, "Subject Review—Malignant Mesothelioma of the Pleura", *Mayo Clin. Proc.*, 63:1234-1244 (Dec., 1988).
J. Morris et al, "Characterization of the Zinc Finger Protein Encoded by the WT1 Wilms' Tumor Locus", *Oncogene*, 6(12):2339-2348 (Dec. 12, 1991).
A. Telerman et al, "Identification of the Cellular Protein Encoded by the Human Wilms' Tumor (WT1) Gene", *Oncogene*, 7(12):2545-2548 (Dec. 12, 1992).
S. Mundlos et al, "Nuclear Localization of the Protein Encoded by the Wilms' Tumor Gene WT1 in Embryonic and Adult Tissues", *Development*, 119:1329-1341 (Dec., 1993).
C. Abate et al, "Expression and Purification of the Leucine Zipper and DNA-Binding Domains of Fos and Jun: Both Fos and Jun Contact DNA Directly", *Proc. Natl. Acad. Sci. USA*, 87:1032-1036 (Feb., 1990).
A. Buckler et al, "Isolation, Characterization, and Expression of the Murine Wilms' Tumor Gene (WT1) During Kidney Development", *Molecular and Cellular Biology*, 11(3):1707-1712 (Mar., 1991).
K. Call et al, "Isolation and Characterizations of a Zinc Finger Polypeptide Gene at the Human Chromosome 11 Wilms' Tumor Locus", *Cell*, 60:509-520 (Feb. 9, 1990).
M. Gessler et al, "Homozygous Deletion in Wilms Tumours of a Zinc-Finger Gene Identified by Chromosome Jumping", *Nature*, 343:774-778 (Feb. 22, 1990).
E. Sevier et al, "Monoclonal Antibodies in Clinical Immunology", *Clin. Chem.*, 27(11):1797-1806 (1981).
M. Co et al, "Humanized Antibodies for Therapy", *Nature*, 351:501-502 (Jun., 1991).
S. Morrison et al, "Chimeric Human Antibody Molecules: Mouse Antigen-Binding Domains with Human Constant Region Domains", *Proc. Natl. Acad. Sci. USA*, 81:6851-6855 (Nov., 1984).

*Primary Examiner*—James C. Housel
*Assistant Examiner*—Susan A. Loring
*Attorney, Agent, or Firm*—Howson and Howson

[57] ABSTRACT

The present invention provides three unique monoclonal antibodies directed against a portion of the Wilms' tumor antigen, and methods of use therefor in detecting, monitoring and diagnosing malignancies characterized by overexpression or inappropriate expression of the WT 1 protein.

4 Claims, 6 Drawing Sheets

FIGURE 2A

| | | | | | | | | | | | | | |
|---|---|---|---|---|---|---|---|---|---|---|---|---|---|
| ATG | AGA | GGA | TCG | CAT | CAC | CAT | CAC | CAC | TCC | ATG | GGT | TCC | 42 |
| Met | Arg | Gly | Ser | His | His | His | His | His | Ser | Met | Gly | Ser | |
| 1 | | | | 5 | | | | 10 | | | | | |

| | | | | | | | | | | | | | |
|---|---|---|---|---|---|---|---|---|---|---|---|---|---|
| GAC | GTT | CGT | GAC | CTG | AAC | GCA | CTG | CTG | CCG | GCA | GTT | CCG | TCC | 84 |
| Asp | Val | Arg | Asp | Leu | Asn | Ala | Leu | Leu | Pro | Ala | Val | Pro | Ser | |
| 15 | | | | | 20 | | | | | 25 | | | | |

| | | | | | | | | | | | | | |
|---|---|---|---|---|---|---|---|---|---|---|---|---|---|
| CTG | GGT | GGT | GGT | GGT | GGT | TGC | GCA | CTG | CCG | GTT | AGC | GGT | GCA | 126 |
| Leu | Gly | Gly | Gly | Gly | Gly | Cys | Ala | Leu | Pro | Val | Ser | Gly | Ala | |
| | | 30 | | | | | 35 | | | | | 40 | | |

| | | | | | | | | | | | | | |
|---|---|---|---|---|---|---|---|---|---|---|---|---|---|
| GCA | CAG | TGG | GCT | CCG | GTT | CTG | GAC | TTC | GCA | CCG | CCG | GGT | GCA | 168 |
| Ala | Gln | Trp | Ala | Pro | Val | Leu | Asp | Phe | Ala | Pro | Pro | Gly | Ala | |
| | | 45 | | | | | 50 | | | | | 55 | | |

| | | | | | | | | | | | | | |
|---|---|---|---|---|---|---|---|---|---|---|---|---|---|
| TCC | GCA | TAC | GGT | TCC | CTG | GGT | GGT | CCG | GCA | CCG | CCG | CCG | GCA | 210 |
| Ser | Ala | Tyr | Gly | Ser | Leu | Gly | Gly | Pro | Ala | Pro | Pro | Pro | Ala | |
| | | | 60 | | | | | 65 | | | | | 70 | |

| | | | | | | | | | | | | | |
|---|---|---|---|---|---|---|---|---|---|---|---|---|---|
| CCG | CCG | CCG | CCG | CCG | CCG | CCG | CCG | CCG | CAC | TCC | TTC | ATC | AAA | 252 |
| Pro | Pro | Pro | Pro | Pro | Pro | Pro | Pro | Pro | His | Ser | Phe | Ile | Lys | |
| | | | | 75 | | | | | 80 | | | | | |

| | | | | | | | | | | | | | |
|---|---|---|---|---|---|---|---|---|---|---|---|---|---|
| CAG | GAA | CCG | AGC | TGG | GGT | GGT | GCA | GAA | CCG | CAC | GAA | GAA | CAG | 294 |
| Gln | Glu | Pro | Ser | Trp | Gly | Gly | Ala | Glu | Pro | His | Glu | Glu | Gln | |
| 85 | | | | | 90 | | | | | 95 | | | | |

| | | | | | | | | | | | | | |
|---|---|---|---|---|---|---|---|---|---|---|---|---|---|
| TGC | CTG | AGC | GCA | TTC | ACC | GTT | CAC | TTC | TCC | GGC | CAG | TTC | ACT | 336 |
| Cys | Leu | Ser | Ala | Phe | Thr | Val | His | Phe | Ser | Gly | Gln | Phe | Thr | |
| | 100 | | | | | 105 | | | | | 110 | | | |

| | | | | | | | | | | | | | |
|---|---|---|---|---|---|---|---|---|---|---|---|---|---|
| GGC | ACA | GCC | GGA | GCC | TGT | CGC | TAC | GGG | CCC | TTC | GGT | CCT | CCT | 378 |
| Gly | Thr | Ala | Gly | Ala | Cys | Arg | Tyr | Gly | Pro | Phe | Gly | Pro | Pro | |
| | | 115 | | | | | 120 | | | | | 125 | | |

| | | | | | | | | | | | | | |
|---|---|---|---|---|---|---|---|---|---|---|---|---|---|
| CCG | CCC | AGC | CAG | GCG | TCA | TCC | GGC | CAG | GCC | AGG | ATG | TTT | CCT | 420 |
| Pro | Pro | Ser | Gln | Ala | Ser | Ser | Gly | Gln | Ala | Arg | Met | Phe | Pro | |
| | | | 130 | | | | | 135 | | | | | 140 | |

| | | | | | | | | | | | | | |
|---|---|---|---|---|---|---|---|---|---|---|---|---|---|
| AAC | GCG | CCC | TAC | CTG | CCC | AGC | TGC | CTC | GAG | AGC | CAG | CCC | GCT | 462 |
| Asn | Ala | Pro | Tyr | Leu | Pro | Ser | Cys | Leu | Glu | Ser | Gln | Pro | Ala | |
| | | | | 145 | | | | | 150 | | | | | |

| | | | | | | | | | | | | | |
|---|---|---|---|---|---|---|---|---|---|---|---|---|---|
| ATT | CGC | AAT | CAG | GGT | TAC | AGC | ACG | GTC | ACC | TTC | GAC | GGG | ACG | 504 |
| Ile | Arg | Asn | Gln | Gly | Tyr | Ser | Thr | Val | Thr | Phe | Asp | Gly | Thr | |
| 155 | | | | | 160 | | | | | 165 | | | | |

FIGURE 2B

| CCC | AGC | TAC | GGT | CAC | ACG | CCC | TCG | CAC | CAT | GCG | GCG | CAG | TTC | 546 |
| Pro | Ser | Tyr | Gly | His | Thr | Pro | Ser | His | His | Ala | Ala | Gln | Phe | |
| | 170 | | | | 175 | | | | | 180 | | | | |

| CCC | AAC | CAC | TCA | TTC | AAG | CAT | GAG | GAT | CCG | GCT | GCT | AAC | AAA | 588 |
| Pro | Asn | His | Ser | Phe | Lys | His | Glu | Asp | Pro | Ala | Ala | Asn | Lys | |
| | | 185 | | | | | 190 | | | | | 195 | | |

| GCC | CGA | AAG | GAA | GCT | GAG | TTG | GCT | GCT | GCC | ACC | GCT | GAG | CAA | 630 |
| Ala | Arg | Lys | Glu | Ala | Glu | Leu | Ala | Ala | Ala | Thr | Ala | Glu | Gln | |
| | | | 200 | | | | | 205 | | | | | 210 | |

TAA 633

FIGURE 3A

```
GTTCAAGGCA GCGCCCACAC CCGGGGGCTC TGCGCAACCC GACCGCCTGT        50

CCGCTCCCCC ACTTCCCGCC CTCCCTCCCA CCTACTCATT CACCCACCCA       100

CCCACCCAGA GCCGGGACGG CAGCCCAGGC GCCCGGGCCC CGCCGTCTCC       150

TCGCCGCGAT CCTGGACTTC CTCTTGCTGC AGGACCCGGC TTCCACGTGT       200

GTCCCGGAGC CGGCGTCTCA GCACACGCTC CGCTCCGGGC CTGGGTGCCT       250

ACAGCAGCCA GAGCAGCAGG GAGTCCGGGA CCCGGGCGGC ATCTGGGCCA       300

AGTTAGGCGC CGCCGAGGCC AGCGCTGAAC GTCTCCAGGG CCGGAGGAGC       350

CGCGGGGCGT CCGGGTCTGA GCCTCAGCAA ATG GGC TCC GAC GTG        395
                                  Met Gly Ser Asp Val
                                   1               5

CGG GAC CTG AAC GCG CTG CTG CCC GCC GTC CCC TCC CTG GGT      437
Arg Asp Leu Asn Ala Leu Leu Pro Ala Val Pro Ser Leu Gly
             10                  15

GGC GGC GGC TGT GCC CTG CCT GTG AGC GGC GCG GCG CAG          479
Gly Gly Gly Cys Ala Leu Pro Val Ser Gly Ala Ala Gln
 20              25                  30

TGG GCG CCG GTG CTG GAC TTT GCG CCC CCG GGC GCT TCG GCT      521
Trp Ala Pro Val Leu Asp Phe Ala Pro Pro Gly Ala Ser Ala
     35                  40                  45

TAC GGG TCG TTG GGC GGC CCC GCG CCG CCA CCG GCT CCG CCG      563
Tyr Gly Ser Leu Gly Gly Pro Ala Pro Pro Ala Pro Pro
         50                  55                  60

CCA CCC CCG CCG CCG CCG CCT CAC TCC TTC ATC AAA CAG GAG      605
Pro Pro Pro Pro Pro Pro Pro His Ser Phe Ile Lys Gln Glu
             65                  70                  75

CCG AGC TGG GGC GGC GCG GAG CCG CAC GAG GAG CAG TGC CTG      647
Pro Ser Trp Gly Gly Ala Glu Pro His Glu Glu Gln Cys Leu
                 80                  85

AGC GCC TTC ACT GTC CAC TTT TCC GGC CAG TTC ACT GGC ACA      689
Ser Ala Phe Thr Val His Phe Ser Gly Gln Phe Thr Gly Thr
 90                  95                 100

GCC GGA GCC TGT CGC TAC GGG CCC TTC GGT CCT CCT CCG CCC      731
Ala Gly Ala Cys Arg Tyr Gly Pro Phe Gly Pro Pro Pro
    105                 110                 115

AGC CAG GCG TCA TCC GGC CAG GCC AGG ATG TTT CCT AAC GCG      773
Ser Gln Ala Ser Ser Gly Gln Ala Arg Met Phe Pro Asn Ala
        120                 125                 130
```

FIGURE 3B

| | | | | | | | | | | | | |
|---|---|---|---|---|---|---|---|---|---|---|---|---|
| CCC | TAC | CTG | CCC | AGC | TGC | CTC | GAG | AGC | CAG | CCC | GCT | ATT | CGC | 815 |
| Pro | Tyr | Leu | Pro | Ser | Cys | Leu | Glu | Ser | Gln | Pro | Ala | Ile | Arg |
|  |  |  | 135 |  |  |  | 140 |  |  |  |  |  | 145 |

```
CCC TAC CTG CCC AGC TGC CTC GAG AGC CAG CCC GCT ATT CGC    815
Pro Tyr Leu Pro Ser Cys Leu Glu Ser Gln Pro Ala Ile Arg
            135             140                     145

AAT CAG GGT TAC AGC ACG GTC ACC TTC GAC GGG ACG CCC AGC    857
Asn Gln Gly Tyr Ser Thr Val Thr Phe Asp Gly Thr Pro Ser
                150                 155

TAC GGT CAC ACG CCC TCG CAC CAT GCG GCG CAG TTC CCC AAC    899
Tyr Gly His Thr Pro Ser His His Ala Ala Gln Phe Pro Asn
160                 165                 170

CAC TCA TTC AAG CAT GAG GAT CCC ATG GGC CAG CAG GGC TCG    941
His Ser Phe Lys His Glu Asp Pro Met Gly Gln Gln Gly Ser
    175                 180                 185

CTG GGT GAG CAG CAG TAC TCG GTG CCG CCC CCG GTC TAT GGC    983
Leu Gly Glu Gln Gln Tyr Ser Val Pro Pro Pro Val Tyr Gly
        190                 195                 200

TGC CAC ACC CCC ACC GAC AGC TGC ACC GGC AGC CAG GCT TTG   1025
Cys His Thr Pro Thr Asp Ser Cys Thr Gly Ser Gln Ala Leu
            205                 210                 215

CTG CTG AGG ACG CCC TAC AGC AGT GAC AAT TTA TAC CAA ATG   1067
Leu Leu Arg Thr Pro Tyr Ser Ser Asp Asn Leu Tyr Gln Met
                220                 225

ACA TCC CAG CTT GAA TGC ATG ACC TGG AAT CAG ATG AAC TTA   1109
Thr Ser Gln Leu Glu Cys Met Thr Trp Asn Gln Met Asn Leu
230                 235                 240

GGA GCC ACC TTA AAG GGA CAC AGC ACA GGG TAC GAG AGC GAT   1151
Gly Ala Thr Leu Lys Gly His Ser Thr Gly Tyr Glu Ser Asp
    245                 250                 255

AAC CAC ACA ACG CCC ATC CTC TGC GGA GCC CAA TAC AGA ATA   1193
Asn His Thr Thr Pro Ile Leu Cys Gly Ala Gln Tyr Arg Ile
        260                 265                 270

CAC ACG CAC GGT GTC TTC AGA GGC ATT CAG GAT GTG CGA CGT   1235
His Thr His Gly Val Phe Arg Gly Ile Gln Asp Val Arg Arg
            275                 280                 285

GTG CCT GGA GTA GCC CCG ACT CTT GTA CGG TCG GCA TCT GAG   1277
Val Pro Gly Val Ala Pro Thr Leu Val Arg Ser Ala Ser Glu
                290                 295

ACC AGT GAG AAA CGC CCC TTC ATG TGT GCT TAC CCA GGC TGC   1319
Thr Ser Glu Lys Arg Pro Phe Met Cys Ala Tyr Pro Gly Cys
300                 305                 310
```

FIGURE 3C

| | | | | | | | | | | | | |
|---|---|---|---|---|---|---|---|---|---|---|---|---|
|AAT|AAG|AGA|TAT|TTT|AAG|CTG|TCC|CAC|TTA|CAG|ATG|CAC AGC|
|Asn|Lys|Arg|Tyr|Phe|Lys|Leu|Ser|His|Leu|Gln|Met|His Ser|
| |315| | | | |320| | | |325| | |

1361

AGG AAG CAC ACT GGT GAG AAA CCA TAC CAG TGT GAC TTC AAG    1403
Arg Lys His Thr Gly Glu Lys Pro Tyr Gln Cys Asp Phe Lys
        330                 335                 340

GAC TGT GAA CGA AGG TTT TCT CGT TCA GAC CAG CTC AAA AGA    1445
Asp Cys Glu Arg Arg Phe Ser Arg Ser Asp Gln Leu Lys Arg
            345                 350                 355

CAC CAA AGG AGA CAT ACA GGT GTG AAA CCA TTC CAG TGT AAA    1487
His Gln Arg Arg His Thr Gly Val Lys Pro Phe Gln Cys Lys
                360                 365

ACT TGT CAG CGA AAG TTC TCC CGG TCC GAC CAC CTG AAG ACC    1529
Thr Cys Gln Arg Lys Phe Ser Arg Ser Asp His Leu Lys Thr
370                 375                 380

CAC ACC AGG ACT CAT ACA GGT GAA AAG CCC TTC AGC TGT CGG    1571
His Thr Arg Thr His Thr Gly Glu Lys Pro Phe Ser Cys Arg
    385                 390                 395

TGG CCA AGT TGT CAG AAA AAG TTT GCC CGG TCA GAT GAA TTA    1613
Trp Pro Ser Cys Gln Lys Lys Phe Ala Arg Ser Asp Glu Leu
        400                 405                 410

GTC CGC CAT CAC AAC ATG CAT CAG AGA AAC ATG ACC AAA CTC    1655
Val Arg His His Asn Met His Gln Arg Asn Met Thr Lys Leu
            415                 420                 425

CAG CTG GCG CTT TGAGGGGTCT CCC                              1680
Gln Leu Ala Leu

WT1 MONOCLONAL ANTIBODIES AND METHODS OF USE THEREFOR

This work was performed with financial support under National Institutes of Health Grant Nos. CA25874, CA52009, CA47983 and CA10815. The United States Government has certain rights in this invention.

CROSS-REFERENCE TO RELATED PATENT APPLICATION

This is a continuation-in-part of co-pending U.S. patent application No. 08/234,783, filed Apr. 28, 1994.

FIELD OF THE INVENTION

This invention relates generally to the field of detecting, monitoring and diagnosing malignancies characterized by expression of the Wilms' tumor 1 antigen.

BACKGROUND OF THE INVENTION

The Wilms' tumor (wt1) gene encodes a protein referred to as WT1 which is expressed in the nucleus of certain cells and possesses the structural features of a DNA binding transcription factor. As illustrated in FIG. 1 below, the WT1 protein is a 429 amino acid protein [SEQ ID NO:4] which contains four contiguous zinc fingers at the carboxyl-terminus, and a glutamine- and proline-rich region at the amino-terminus. The amino-terminal region of WT1 protein mediates transcriptional suppression or activation in transient transfection assays [Madden et al, Science, 253:1550–1553 (1991); Maheswaran et al, Proc. Natl. Acad. Sci. USA, 90:5100–5104 (1993); S. L. Madden et al, Oncogene, 8:1713–1720 (1993)]. Splice variants of WT1 can produce the protein with a 17 amino acid insert at amino acid 249 and/or a 3 amino acid insert at amino acid 390.

The wt1 gene encoding WT1 protein is located on chromosome 11p13 and has been found to be mutated or deleted in a subset of hereditary and sporadic Wilms' tumors. Recently, high levels of wt1 expression were reported in a variety of tumors such as ovarian carcinomas [Bruenig et al, Cancer Invest., 11:393–399 (1993)], prostate cancer, mesotheliomas [Park et al, cited above], and leukemias [Miwa et al, Leukemia, 6:405–409 (1992), Miyagi et al, Leukemia, 7:970–977 (1992)].

Diagnostic methods for the ovarian carcinomas, mesotheliomas, and leukemias referred to above are based primarily on clinical attributes and histology of tumor specimens. These methods may at times not distinguish between closely related diseases and may lead to inappropriate treatments of patients. For example, in addition to the presence of many histological variants of malignant mesothelioma, there are other lesions that can affect the pleural surface and present a clinical and histological picture quite similar to malignant mesothelioma [R. J. Pisani et al, Mayo Clin. Proc., 63:1234–1244 (1988)]. Additional relatively specific molecular markers that clearly distinguish between clinically similar lesions for malignant mesotheliomas as well as the other cancers would thus be a valuable clinicopathological tool which will permit a precise diagnosis. This is important since treatment protocols and prognosis for such conditions vary significantly.

Currently available diagnostic tools include rabbit polyclonal antibodies for WT1 protein known in the art. Morris et al, Oncogene, 6:2339–2348 (1991) describe two such antibodies which recognize amino acid fragments spanning amino acids 294–429 of SEQ ID NO:4 and amino acids 85–173 of SEQ ID NO:4, respectively, of the WT1 protein. Another rabbit polyclonal antibody, which recognizes WT1 amino acids 275–429 of SEQ ID NO: 4 was described by Telerman et al, Oncogene, 2545–2548 (1992). Still other WT1 polyclonal antibodies are commercially available, e.g. the rabbit polyclonal antibody SC-192, which is available from Santa Cruz. However, while polyclonal antibodies in general are able to detect WT1 expression, they have disadvantages in their potential for cross-reactivity with closely related proteins which share common domains with the WT1 protein. These polyclonal antibodies by their nature are likely to provide inconsistent results in antigen specificity and binding affinity studies and are not particularly desirable for diagnostic uses.

Additionally, a commercially available mouse monoclonal antibody, DG-10 (Applied BioTechnology) was raised to the zinc finger region of WT1 and is known to cross-react with the Egr1 proteins. Expression of Egr1 proteins is not limited to cells or tissues that express WT1 and is independently regulated from WT1 expression. Therefore, any antibodies raised to the zinc finger domain in the carboxyl terminus of WT1 may not be useful for selective detection of the WT1.

Another anti-WT1 mouse monoclonal antibody has been described by Mundlos et al, Development, 119:1329–1341 (1993). The Mundlos et al antibody is specific for a 17 amino acid sequence insert (See FIG. 1 below), i.e., a splice variant, that is present in only a subpopulation of the alternatively spliced WT1 mRNA messages.

Thus, there exists a need in the art for methods and compositions for detecting and differentially diagnosing conditions characterized by over-expression or inappropriate expression of WT1.

SUMMARY OF THE INVENTION

In one aspect, the present invention provides a hybridoma cell line secreting a monoclonal antibody (MAb) specific for a protein antigen, referred to as WT1-6F [SEQ ID NO: 2], which contains amino acids 1–181 of WT1 [SEQ ID NO: 4]. One such cell line is an H2-secreting line, deposit designation ATCC No. 11598. Another cell line which is an embodiment of this aspect is the H7-secreting line, deposit designation ATCC No. 11599. Still a third cell line is the HC17-secreting line, deposit designation ATCC No. 11600.

In another aspect, the present invention provides a monoclonal antibody produced by a cell line described above. Three such antibodies, designated H2, H7 and HC17 are described herein.

In yet another aspect, the invention provides the heavy chain and light chain variable region polypeptides of the MAbs of the invention, and other fragments thereof, such as Fab fragments, F(ab)$_2$ fragments, Fv fragments and the like.

In still another aspect, the present invention provides methods of diagnosing malignancies characterized by over-production or inappropriate expression of WT1 protein. These methods involve screening biological samples with antibodies of the invention, described above.

In a further aspect, the present invention provides methods of monitoring treatment of conditions characterized by over-production or inappropriate expression or production of WT1 protein. One embodiment of such a method involves monitoring leukemia treatment, particularly determining the level of active leukemia following a treatment cycle.

In another aspect, the present invention provides methods for differentiating between malignancies characterized by over-production or inappropriate expression of WT1 protein and conditions having similar symptomatic profiles. One embodiment of such a method involves distinguishing between mesotheliomas and conditions characterized by inflammatory reactions.

In a still another aspect, the present invention provides kits useful for detecting, monitoring, and/or diagnosing a disease characterized by the expression of the Wilms' tumor antigen comprising a MAb raised against the WT-6F antigen [SEQ ID NO: 2]. Desirably, the H2, H7, HC17 MAbs or a cocktail of these, is included in such a kit.

Other aspects and advantages of the present invention are described further in the following detailed description of the preferred embodiments thereof.

BRIEF DESCRIPTION OF THE DRAWINGS

FIGS. 2A–2B provides the nucleic acid and amino acid sequences of the WT-6F antigen [SEQ ID NOS: 1 and 2] in which amino acids 1–11 represent a histidine fusion protein to facilitate purification; amino acids 12–192 are amino acids 1–181 of the WT1 protein; and amino acids 193–210 of SEQ ID NO: 2 are vector sequences added during cloning.

FIGS. 3A–3C provides the nucleotide and amino acid sequences of the full length WT1 protein [SEQ ID NOS: 3 and 4]. The 3' non-coding sequence of the mRNA is omitted in this figure.

DETAILED DESCRIPTION OF THE INVENTION

Figure 1:
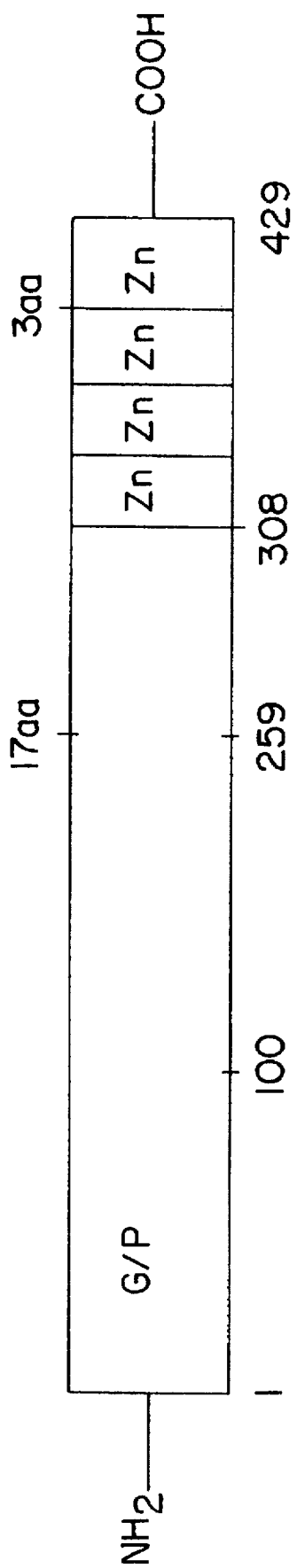
FIG. 1 is a schematic diagram of the Wilms' tumor protein functional domains. The WT1 protein contains two discrete functional domains: the amino terminus contains a transcriptional regulator domain and the carboxy terminus contains a DNA binding domain with four $C_2H_2$ zinc fingers. G/P refers to the glutamine- and proline-rich region at the amino-terminus; ZN refers to four contiguous zinc fingers at the carboxyl-terminus. Alternatively spliced transcripts of WT1 are produced which insert 17 amino acids, VAAGSSSSVKWTEGQSN, [SEQ ID NO: 7] (17AA) within the transcriptional regulatory domain (at amino acid 249 of SEQ ID NO: 4) or a tripeptide encoding the amino acid KTS within the DNA binding domain (at amino acid 390 of SEQ ID NO: 4) between zinc fingers 3 and 4. The significance of the alternatively spliced WT1 transcripts is not known.

The present invention provides hybridomas secreting monoclonal antibodies (MAbs) specific for epitopes found in the amino terminal amino acids 1–181 of the Wilms' tumor (WT1) protein [SEQ ID NO: 4]. The MAbs of this invention are useful in identifying, monitoring and diagnosing conditions characterized by over-expression or inappropriate expression of the WT1 protein. The MAbs do not cross-react with the ubiquitous and closely related early growth response (Egr1) family of proteins which share approximately 50% homology within the DNA binding domain located in the carboxyl terminal amino acids 275–429 of WT1 [SEQ ID NO:4]. Therefore, when used in a diagnosis based on the detection of WT1 protein, the MAbs of this invention eliminate false positives currently produced in detection methods by the use of currently available WT1 antibodies which are specific for epitopes in the zinc finger domain of the protein.

I. Definitions

As used herein "functional fragment" is a partial complementarity determining region (CDR) sequence or partial heavy or light chain variable sequence of an antibody which retains the same antigen binding specificity and/or neutralizing ability as the antibody from which the fragment was derived.

A "condition characterized by over-expression or inappropriate expression of WT1" refers to a cancer or other abnormal physiological state which exhibits an increased level of expression of WT1 or exhibits expression of a mutant WT1 protein, or exhibits expression of WT1 protein where such expression should normally not occur. Such increased WT1 expression has been detected in cells derived from ovarian carcinomas, mesotheliomas, prostate cancer and leukemias. Ordinarily, in normal tissues, WT1 protein is absent or present in such low levels that it cannot be detected using conventional techniques, such as northern blot hybridization or reverse transcriptase polymerase chain reaction (RT-PCR). In contrast to WT1 protein, when a patient exhibits a "condition characterized by over-expression or inappropriate expression of WT1" as defined herein, the presence of WT1 protein can be detected using the reagents of the invention and standard techniques, e.g. immunohistochemical procedures, including immunoblotting and immunofluorescence, Western blot analysis, and enzyme-linked immunosorbant assay (ELISA). The presence of WT1 mRNA in such patients can be detected using Northern blot analysis or RNA reverse transcription PCR techniques. Background levels of WT1 can be determined by measuring such levels in the tissues where WT1 is not normally expressed (as described above) in persons not afflicted with disease.

"CDRs" are defined as the complementarity determining region amino acid sequences of an antibody. CDRs are contained within the hypervariable regions of immunoglobulin heavy and light chains. CDRs provide the majority of contact residues for the binding of the antibody to the antigen or epitope. CDRs of interest in this invention are derived from donor antibody variable heavy and light chain sequences, and include functional fragments and analogs of the naturally occurring CDRs, which fragments and analogs also share or retain the same antigen binding specificity and/or neutralizing ability as the donor antibody from which they were derived.

By 'sharing the antigen binding specificity or neutralizing ability' is meant, for example, that although a given MAb may be characterized by a certain level of antigen affinity, and a CDR encoded by a nucleic acid sequence of the same MAb in an appropriate structural environment may have a lower or higher affinity, it is expected that CDRs of that MAb in such environments will nevertheless recognize the same epitope(s) as the MAb from which they are derived.

A "monoclonal antibody" refers to homogenous populations of immunoglobulins which are capable of specifically binding to WT1 protein. It is understood that WT1 protein may have one or more antigenic determinants, particularly in the amino acid sequence spanning amino acids 1–181 of SEQ ID NO: 4. The antibodies of the invention may be directed against one or more of these determinants. As used herein, a "cocktail" of these antibodies comprises any combination of the antibodies of the invention.

A "chimeric antibody" refers to a type of engineered or recombinantly produced antibody which contains naturally-occurring variable region light chain and heavy chains (both CDR and framework regions) derived from a non-human donor antibody, such as the MAbs described herein, in association with light and heavy chain constant regions derived from a human (or other heterologous animal) acceptor antibody.

A "humanized antibody" refers to a recombinantly produced antibody having its CDRs and/or other portions of its light and/or heavy variable domain framework regions derived from a non-human donor immunoglobulin, such as the MAbs of the present invention, the remaining immunoglobulin-derived parts of the molecule being derived from one or more human immunoglobulins. Such antibodies can also include a humanized heavy chain associated with a donor or acceptor unmodified light chain or a chimeric light chain, or vice versa.

A "bi-specific antibody" refers to an antibody derived from the Fab portions of two parent antibodies, each of which binds a separate antigen. The bi-specific antibody is characterized by the ability to bind to two antigens, particularly, the antigens to which the parent antibodies bound.

A Fab fragment refers to a polypeptide containing one entire light chain and amino terminal portion of one heavy chain from an antibody, such as the MAbs of this invention. A F(ab')$_2$ fragment refers to the fragment formed by two Fab fragments bound by disulfide bonds.

II. Hybridoma Cell Lines and MAbs of the Invention

The hybridoma cell lines and monoclonal antibodies of the invention are produced by employing as antigen, a novel WT1-derived protein antigen, which contains only the N-terminal sequence of the WT1 protein. Desirably, the invention employs as an immunogen a WT1 containing protein antigen, referred to as WT1-6F [SEQ ID NO: 2], which contains amino acids 1-181 of the N-terminus of the native human WT1 sequence (see FIG. 1 and SEQ ID NO: 4). This antigen has been developed by the inventors and does not contain any of the zinc-finger region characteristic of the carboxyl terminal portion of the WT1 protein or any of the 17 amino acid insert of the splice variant of the protein (see FIG. 1). Additional details relating to the preparation and expression of the 6F antigen are provided in Example 1 below.

Generally, the hybridoma process involves generating a B-lymphocyte to the selected antigen, which B lymphocyte produces a desired antibody. Techniques for obtaining the appropriate lymphocytes from mammals injected with the target antigen, WT1-6F, are well known. Generally, the peripheral blood lymphocytes (PBLs) are used if cells of human origin are desired. If non-human sources are desired, spleen cells or lymph nodes from other mammalian sources are used. A host animal, e.g. a mouse, is injected with repeated doses of the purified antigen, and the mammal is permitted to generate the desired antibody producing cells.

Thereafter the B-lymphocytes are harvested for fusion with the immortalizing cell line. Immortalizing cell lines are usually transformed mammalian cells, particularly cells of rodent, bovine and human origin. Most frequently, rat or mouse myeloma cells are employed. Techniques for fusion are also well known in the art and generally involve mixing the cells with a fusing agents, e.g. polyethylene glycol.

Immortalized hybridoma cell lines are selected by standard procedures, such as HAT selection. From among these hybridomas, those secreting the desired monoclonal antibody are selected by assaying the culture medium by standard immunoassays, such as Western blotting, ELISA, or RIA. Antibodies are recovered from the medium using standard purification techniques. See, generally, Sambrook et al, *Molecular Cloning: A Laboratory Manual*, 2nd edit., Cold Spring Harbor Laboratory, Cold Spring Harbor, N.Y. (1989). Alternatively, non-fusion techniques for generating an immortal antibody-producing hybridoma cell line may be employed to generate a hybridoma antibody, where possible, e.g. virally induced transformation.

The invention provides three exemplary hybridoma cell lines and the MAbs secreted therefrom produced using WT1-6F as the antigen. See Examples 2 and 3 below. These three hybridomas secrete antibodies termed H2, H7 and HC17, respectively. Each hybridoma was deposited with the American Type Culture Collection, 12301 Parklawn Drive, Rockville, Md. 20852, U.S.A. ("ATCC") on Mar. 31, 1994, pursuant to the provisions of the Budapest Treaty. The H2-secreting hybridoma was granted accession number ATCC 11598, the H7-secreting hybridoma was granted accession number ATCC 11599, and the HC17-secreting hybridoma was granted accession number ATCC 11600.

The H2, H7 and HC17 antibodies are murine IgG$_1$ antibodies, and have been demonstrated to specifically bind WT1 protein and not to cross-react with the closely-related Egr1 family of proteins. All three monoclonal antibodies recognize the recombinant protein in ELISA assays, and full length WT1 protein in immuno-precipitation and Western blot analysis. Preliminary analysis suggests that at least two distinct epitopes in the WT1-6F protein are recognized by the three MAbs. The MAbs of this invention are characterized in more detail in Example 4 below.

A Western blot analysis was performed to test the ability of the three MAbs to detect two recombinant proteins: 6F [SEQ ID NO: 2] which contains WT1 amino acids 1-181 of SEQ ID NO: 4, and WT91 which contains WT1 amino acids 85-173 of SEQ ID NO: 4. All three MAbs detect the 6F recombinant protein [SEQ ID NO: 2] containing WT1 amino acids 1-181. However, only H2 and H7 detect the WT91 recombinant protein containing amino acids 85-173 of WT1, suggesting that H2 and H7 recognize an epitope within the WT1 amino acid sequence 85-173 and HC17 recognizes an epitope outside this region.

These MAbs are useful as diagnostic reagents, and possibly as therapeutic reagents as described in more detail below.

III. MAb Antibody Fragments

The present invention also includes functional fragments of the MAbs defined above, preferably those derived from the H2, H7 and/or HC17 MAbs of the invention. Such functional fragments include the heavy chain and light chain variable region polypeptides of the MAbs of the invention, and other fragments thereof, such as Fab fragments, F(ab)$_2$ fragments, Fv fragments and the like.

These fragments are useful as diagnostic reagents and as donors of sequences, including the variable regions and CDR sequences, useful in the formation of recombinant, chimeric, humanized or bi-specific antibodies. Techniques for generating such antibodies and antibody fragments are known in the art. For example, the functional fragments of the invention may be obtained using conventional genetic engineering techniques. See, generally, Sambrook et al., cited above. Alternatively, desired portions thereof, e.g. the CDR sequences, may be chemically synthesized.

These antibody functional fragments are useful in the assays of the invention to diagnose WT1 over-expression or inappropriate expression in specific tumors, which assays are described in more detail below. For example, by conjugating these antibody fragments to enzymes, such as horseradish peroxidase, these fragments may be employed in a conventional one-step detection assay.

IV. Diagnostic Reagents and Kits

The invention includes kits of reagents for use in immunoassays, particularly sandwich immunoassays. Such kits include a solid phase support, a monoclonal antibody of the invention, a functional fragment thereof, or a cocktail thereof, and means for signal generation. The antibodies of the invention may be pre-attached to the solid support, or may be applied to the surface of the solid support when the kit is used. The signal generating means may come pre-associated with an antibody of the invention or may require combination with one or more components, e.g. buffers, antibody-enzyme conjugates, enzyme substrates, or the like, prior to use. Kits may also include additional reagents, e.g. blocking reagents for reducing nonspecific binding to the solid phase surface, washing reagents, enzyme substrates, and the like. The solid phase surface may be in the form of microtiter plates, microspheres, or other materials suitable for immobilizing proteins. Preferably, an enzyme which catalyzes the formation of a chemiluminescent or colored product is a component of the signal generating means. Such enzymes are well known in the art.

Such kits are useful in the detection, monitoring and diagnosis of conditions characterized by over-expression or inappropriate expression of the WT1 protein.

V. Diagnostic Assays

The MAbs, fragments, reagents and kits of the invention may be used with standard assay formats for the identification and diagnosis of conditions characterized by WT1 expression, over-expression or inappropriate expression, particularly in tumor/leukemic cells. The detection and measurement of WT1 expression in tissue that does not normally express WT1 or over-expression or inappropriate expression in tissue that does normally express WT1 may be accomplished by resort to several known techniques, e.g., immunofluorescence (detection of WT1 protein in fixed cells/tissues) and detection of WT1 protein of whole cell extracts by western analysis. Most particularly, the MAbs and other compositions of this invention may be used to detect WT1 expression in abnormal kidney and genitourinary development and cancers which over-express WT1, particularly, leukemias, mesothelioma, granulosoma, prostate and ovarian cancers. The reagents of the invention may also be used to monitor therapy of such conditions.

Desirably, the MAbs and fragments thereof, when used as diagnostic reagents are conventionally labelled for use as molecular weight markers or for use in ELISAs, immunofluorescence, and other conventional assay formats for the measurement of WT1 in an appropriate biological sample. Suitable label systems are well known to those of skill in the art and include fluorescent compounds, radioactive compounds or elements, and a variety of enzyme systems. As used herein, suitable samples include, without limitation, whole blood, serum, plasma, tissue samples, bone marrow, and urine.

Advantageously, the MAbs of the invention can be used to screen for the WT1 protein using standard antibody staining techniques, e.g. the avidin-biotin system, immunofluorescence, or the like. For example, a tissue, e.g. from a biopsy, is fixed on a slide using standard techniques. A selected MAb (or fragment thereof) of the invention is then applied to the slide and incubated under standard conditions, e.g. at room temperature for about 1 hour. A labelled anti-mouse antibody is then used for detection. Parallel experiments with positive and negative controls (minus MAb of invention) are performed.

Significantly, if the MAbs of the invention avoid interference with MAb recognition by fixation of the tumor tissue with conventional reagents, e.g. paraformaldehyde and, preferably, methanol, these antibodies may be useful on routine pathology slides. For example, the ability of these monoclonal antibodies to detect prostate cancer cells has been demonstrated. Preliminary data has demonstrated that cocktails of these antibodies, e.g., H2/HC17 and H7/HC17, are particularly well suited for this purpose.

The MAbs, or functional fragments thereof, of the invention are useful in the detection of a condition characterized by over-expression of WT1 antigen, including leukemias, mesothelioma, and granulosoma, or to differentiate such a condition from other conditions which exhibit similar clinical symptoms. For example, a Mab of the invention can differentiate a mesothelioma from other pleural tumors; such a use is clinically significant in view of the different prognoses for pleural tumors of non-adenocarcinoma origin and adenocarcinomas. Such a method involves obtaining a suitable biological sample from a patient, incubating the sample in the presence of a Mab or functional fragment thereof of the invention, and detecting the presence of binding of the Mab or fragment to the biological sample. The presence of binding above background levels detected in a non-WT1 expressing normal tissue sample indicates the presence of a mesothelioma. Any tissue or established cell line which does not express WT1 MRNA may serve as a standard for negative expression of WT1 protein, including those described above in the background.

Alternatively, the Mabs and fragments thereof of the invention are useful to monitor a course of treatment for a condition characterized by over-expression or inappropriate expression of the WT1 antigen. For example, active leukemia (e.g. in blast crisis) cells express WT1, while inactive leukemic cells do not express WT1. Thus, during or following a treatment cycle, a biological sample from the leukemia patient is periodically tested in an assay of the invention to monitor residual leukemic disease. The lack of, or reduction of levels of, binding of a Mab or fragment of the invention to the sample indicates that the course of treatment, e.g., chemotherapy, is successful in reducing the tumor or cancer. Similarly, the MAbs and fragments of the invention may be used to detect leukemic blast cells in purged or unpurged hematopoietic stem cell preparations intended for use in bone marrow transplantation.

It is anticipated that one of skill in the art of diagnostic assays may devise other series of steps utilizing the Mabs or fragments of this invention to accomplish the detection of levels of WT1 expression indicative of disease. Such assay formats are known within the art, and are simply a matter of selection. This invention is not limited by the particular assay format or assay steps employed in the diagnosis of inappropriate expression of WT1 protein in biological samples.

Because the Mabs H2, H7, and HC17 were raised to a region of the WT1 amino acid sequence that is unique to the amino terminal portion of WT1 and does not contain the zinc finger DNA binding domains, these Mabs and fragments have little potential for crossreactivity with non-WT1 proteins, unlike known other WT1 polyclonal and monoclonal Mabs. For example, these Mabs do not cross-react with the Egr family of proteins. Thus they permit an unambiguous positive detection of WT1 expression in biological samples.

The advantages of using these Mabs for such diagnosis in comparison to the use of the known monoclonal and polyclonal antibodies of the art rely in the defined specificity of the Mabs for the amino terminal sequence of WT1, their uniform binding affinity and their lack of cross-reactivity as described above.

V. Therapeutic Use of Mabs of this Invention

Further, if these Mabs of the invention are have the ability to internalize into the nucleus of the cell which expresses WT1 [see, e.g., U.S. Pat. No. 5,296,348, issued Mar. 22, 1994, incorporated by reference herein], they may also be employed in the treatment of such WT-1 expressing tumors or cancers. For example, these Mabs, other antibody types such as chimeric or humanized antibodies, or fragments which share the binding affinity or specificity of the whole Mab may be used to deliver toxins or therapeutic agents to the tumor or metastasis sites.

These Mabs, other antibodies and fragments of the present invention may also be employed in other therapeutic methods known to those of skill in the art.

The following examples illustrate the characterization and uses of the antibodies of the invention. These examples are illustrative only and do not limit the scope of the invention.

EXAMPLES 1—PREPARATION OF THE WT1–6F ANTIGEN

A. Cloning Strategy

A recombinant protein containing the first 181 amino acids of the human WT1 was produced to use as an antigen in the preparation of WT1 specific antibodies as follows.

The amino terminus of WT1 was subcloned from 7Zf+ WT1, a synthetic full-length human WT1 nucleotide sequence described in Morris et al. cited above. Briefly, the nucleotide sequence encoding the full-length protein was constructed from the partial human WT1 cDNA clone WT33 [Call et al, Cell, 60:509–520 (1990)]. The WT1 amino acids 1–84 plus an overlapping 20 amino acid segment were synthesized using overlap-extension polymerase chain reaction. The nucleotides specifying amino acid codons were optimized for expression in E. coli.

The resulting synthetic DNA fragment (320 bp) was fused to the 5' end of WT33 at a unique Bst XI site centered at position WT1 amino acid 101 of SEQ ID NO: 4 (nucleotide 50 of WT33). A Cla I-Eco RI fragment was subcloned into pGem7Zf+ (Promega, Madison, Wis.) to produce 7Zf+WT1. From this plasmid, a Ico I-Bam HI fragment was isolated and subcloned into a modified pet11d vector (Novagen, Madison, Wis.).

The pet11d vector was modified by digesting with Nco I and ligating to synthetic, double-stranded oligonucleotides which contained the following 5' overhangs complementary to a Nco I restriction site to produce 6XHISpet11d:

5'-CATGAGAGGATCGCATCACCATCACCATCACTC 3'[SEQ ID NO: 5]
3'TCTCCTAGCGTAGTGGTAGTGGTAGTGAGGTAC-5' [SEQ ID NO: 6].

The synthetic oligonucleotide introduces nucleotide codons that encode the amino acids MRSHHHHHH of SEQ ID NO: 2 to produce an in-frame 5' hexa-histidine fusion protein that maintains a single Nco I restriction site at the 3' end of the sequence. The 5' hexa-histidine encoding region facilitates protein purification [Abate et. al., Proc. Natl. Acad. Sci. USA, 87:1032 (1990)].

The Nco I-Bam HI fragment of 7Zf+WT1 containing the amino terminus of WT1 was subcloned into 6XHISpet11d digested with Nco-I and Bam HI to create pet11d-6F.

B. Expression in E. coli and Purification

The bacterial strain BL21 (Novagen, Madison, Wis.) was transformed with the pet11d-6F DNA. Protein expression was induced in a logarithmically growing bacterial culture with 1 mM isopropyl-β-thiogalacto-pyranoside (IPTG) for two to three hours at 37° C. Bacteria were harvested by centrifugation, lysed in 6M guanidine-HCl, 50 mM sodium phosphate, pH 8.0 for 2 hours at room temperature or overnight at 4° C., and clarified by centrifugation at 40,000×g for 30 minutes.

The histidine fusion recombinant protein WT1–6F was purified by a one step affinity binding of the hexa-histidines to the nickel-chelate affinity resin NTA-agarose (Qiagen, Chatsworth, Calif.) using recommended procedures. The purified protein was renatured by dialysis into phosphate buffered saline with 5% glycerol.

Purity of the protein was determined by sodium dodecyl sulfate-polyacrylamide gel electrophoresis (SDS-PAGE) as follows. The purified protein was renatured by dialysis into PBS containing 5% glycerol and analyzed on a 10% SDS polyacrylamide gel. Proteins were stained with Coomassie blue. The 6F recombinant protein was shown to be homogenous, migrating under denaturing conditions as a 28 kDa protein.

C. The WT1–6F Antigen

The 6F amino acid sequence is encoded by a synthetic nucleotide sequence shown in FIG. 2 [SEQ ID NOS: 2 and 1]. The 6F nucleotide sequence was derived from the synthetic full-length human WT1 sequence [Morris et al. cited above and SEQ ID NOS: 3 and 4]. As illustrated in FIG. 2, the recombinant 6F antigen contains amino acids 1–181 of the human WT1 sequence [SEQ ID NO:4] as well as amino acids at both the amino and carboxyl ends, which sequences were introduced during cloning. The entire 6F amino acid sequence is shown in FIG. 2 [SEQ ID NO: 2]. Amino acids 1–11 (MRGSHHHHHHS) of SEQ ID NO: 2 were added to produce a histidine fusion protein to facilitate purification of the recombinant protein. Amino acids 193–210 of SEQ ID NO: 2 are not WT1 sequences, but were added from the vector during cloning. Note that nucleotides 1–333 [SEQ ID NO: 1] are synthetic sequences optimized for protein translation in E. coli; the remaining nucleotides are derived from the human WT33 cDNA clone. This does not change the human WT1 amino acid sequence, but increases efficiency of protein expression in E. coli [Rauscher et al, Science, 250:1259–1262 (1990), Abate et. al., Proc. Natl. Acad. Sci., 87:1032–1036 (Feb. 1990)].

A second recombinant protein, WT91 (described in Morris et al. cited above) contains the amino acids 85–173 of SEQ ID NO: 4.

EXAMPLE 2—PREPARATION OF ANTISERA AND IMMUNIZATION

Rabbit polyclonal antisera was produced by CoCalico Biologicals, Inc. Rabbits were immunized subcutaneously with 100 μg of 6F recombinant protein of Example 1 and boosted at two to three week intervals. The rabbit sera was used without further purification.

EXAMPLE 3—PREPARATION OF MONOCLONAL ANTIBODIES

Fifty micrograms of purified recombinant protein of Example 1 was injected subcutaneously into the hind footpads of BALB/c mice every two weeks for a total of three injections. Sera was collected from the tail, and tested for WT1 specific antibodies by immuno-precipitation of 35S-methionine labeled in vitro translated human WT1 protein.

Two weeks later, 50 μg of protein in 200 μl of saline was injected intravenously followed by removal of each animal's spleen. Spleen cells were fused with a myeloma cell line, P3X63AG8/653 [ATCC CRL 1580], using standard techniques.

The resulting hybridomas producing MAbs H2, H7 and HC17 were screened in a two step process. Positive clones were initially identified using an enzyme-linked immunosorbent assay (ELISA) against the 6F recombinant protein. Secondary screening was carried out using immunoprecipitation of full length WT1 protein produced by in vitro translation (IVT). These experiments demonstrated that the MAbs H2, H7 and HC17 specifically recognize the WT1 protein and that they appear to recognize distinct epitopes on the WT1 protein.

1. Immunoprecipitation

Full length WT1 was expressed in vitro from by transcribing RNA from Eco RI linearized vector 7Zf+WT1 with SP6 RNA polymerase, and translating protein in rabbit reticulocyte lysate with $^{35}$S-methionine. The $^{35}$S-methionine labeled protein is 55 kDa and is specifically immunoprecipitated by rabbit polyclonal anti-6F sera, and by the mouse monoclonal antibodies H2, H7, and HC17.

Immunoprecipitations were done as previously described in Morris et al, cited above. Briefly, IVT WT1 was added to radioimmunoprecipitation buffer with protease inhibitors (RIPA: 10 mM Tris-Cl pH 7.4, 150 mM sodium chloride, 1 mM ethylenediamine-tetraacetic acid (EDTA), 1% Triton X-100, 1% deoxycholate, 0.1% SDS, 0.1 mMphenylmethylsulfonic acid (PMSF), 2 µg/ml leupeptin and 2 µg/ml aprotinin) along with antibodies and incubated 90 minutes at 4° C. Either 30 µl of 10% Staphylococcus A (Pansorbin, Calbiochem, San Diego, Calif.) or 100 µl of 50% Protein A Sepharose (Pharmacia, Piscataway, N.J.) was added and incubated for 15 minutes (Staph A) or 30 minutes (Protein A). The immune complexes were collected by centrifugation in the microfuge and washed with 0.5–1.0 ml of RIPA 3 to 4 times. The immunoprecipitated proteins were analyzed on 10 or 15% SDS-polyacrylamide gels and visualized by autoradiography.

The resulting SDS PAGE gel demonstrated that MAbs of this invention immunoprecipitate WT1 expressed by in vitro transcription and translation.

2. Baculovirus expression of full length WT1

The full length WT1 protein encoding sequence was subcloned from 7Zf+WT1 into a baculovirus expression vector. Sf9 insect cells were infected with WT1-baculovirus and cells harvested 48–96 hours following infection. Cells were pelleted by centrifugation, washed three times in PBS. Whole cell lysates were prepared by lysing a cell pellet in 10 times the cell pellet volume with Laemmli loading buffer (50 mM Tris-Cl, pH 6.8, 100 mM dithiothreitol, 2% SDS, 0.1% bromophenol blue, 10% glycerol).

Ten µl of WT1 lysate were analyzed on a 10% SDS-polyacrylamide gel. Western analysis of protein was performed as follows. A whole cell lysate of Sf9 cells expressing baculovirus encoded WT1 protein was separated on a 10% SDS-polyacrylamide gel and transferred to 0.45 µm BA 85 nitrocellulose (Schleicher and Schuell, Keene, N.H.) using semi-dry electroblot transfer for 60–90 minutes at 4 mAmps/cm$^2$. Molecular weight standards were cut from the blot and stained with Amido black and the nitrocellulose filter blot was blocked in 5% BSA-PBS for 60 minutes at room temperature or overnight at 4° C. The primary antibody was diluted in blocking buffer (rabbit anti-6F 1:400; the monoclonal antibodies of the invention 1:500 or 1:1000) and added to filters for 30 to 60 minutes at room temperature.

Filters were rinsed briefly twice in wash buffer (PBS, 0.1% BSA, 1% Tween 20) and three times for 10 minutes each while shaking vigorously. Soluble protein A conjugated to horseradish peroxidase (Amersham, Arlington Heights, Ill.) was diluted 1:5000 in 5% BSA-PBS and incubated for 30 minutes at room temperature. Filters were washed as before, rinsed in PBS, and incubated with a 1:1 mixture of the ECL substrates A and B (Amersham, Arlington Heights, Ill.) for 1 minute at room temperature. Filters were removed from the liquid, excess moisture drained, and wrapped in Saran wrap and immediately exposed to film (average exposure 15 seconds to 3 minutes).

The gels revealed that the polyclonal and monoclonal antibodies of this invention specifically detect a 55 kDa protein in Sf9 cells transfected with WT1 baculovirus expression vector and not cells mock transfected.

EXAMPLE 4—CHARACTERIZATION OF MURINE MABS H2, H7 AND HC17

To determine whether the WT1 monoclonal antibodies of the present invention detect different epitopes within the first 181 amino acid of the 6F antigen, purified recombinant proteins 6F (WT1 amino acid 1–181) and WT91 (WT1 amino acid 85–173) were separated on a 15% SDS-polyacrylamide gel and transferred to nitrocellulose. Western blot analysis was performed as described in Example 3.

Polyclonal antibodies were diluted 1:400 and monoclonal antibodies diluted 1:500. The polyclonal antisera recognizes both the 6F and WT91 recombinant proteins. The monoclonal antibodies H2 and H7 recognize both 6F and WT91 recombinant proteins, suggesting they detect an epitope with amino acid 85–173 of WT1 [SEQ ID NO:4]. HC17 does not detect the WT91 recombinant protein indicating that it recognizes an epitope outside of this region.

EXAMPLE 5—DETECTION OF WT1 PROTEIN IN HUMAN ACUTE LEUKEMIAS

The following study demonstrates that a MAb of the invention, H2, is able to distinguish between leukemic blast cells and normal mononuclear cells by detecting the WT1 protein in nuclei of leukemic blast cells. No WT1 protein was detected in the nuclei of normal mononuclear cells or mononuclear cells by either immunofluorescence or by conventional reverse-transcriptase polymerase chain reaction (RT-PCR) techniques.

A. Samples

Mononuclear cell preparations of 110 adult leukemia patients were examined in this study. T-cell acute lymphoblastic leukemias (T-ALL) had been diagnosed in 27, common acute lymphoblastic leukemias (c-ALL) in 28, pre-pre-B cell acute lymphoblastic leukemias (ppB-ALL) in 8, acute myelogenous leukemias (AML) in 40, chronic myelogenous leukemias in blast crisis (one lymphatic and three myeloid CML-BC) in 4 and chronic myelogenous leukemias in chronic phase (CML-CP) in 3 patients. Controls were 4 patients with reactive bone marrow aspirates who had fever of unknown origin (H.M., G.S.), anemia secondary to iron deficiency (V.H.) or limited-disease esophageal cancer with no morphological evidence of bone marrow infiltration (H.F.).

Mononuclear cells were isolated from bone marrow aspirates or in a few cases from peripheral blood samples by Ficoll-Hypaque density gradient centrifugation (Pharmacia, Freiburg, Germany). Also, peripheral mononuclear cells enriched with CD34$^+$hematopoietic progenitors were obtained from five patients (S.K., S.Kt., K.D., N.G., H.G.) who had solid cancer with no morphological evidence of bone marrow infiltration. Their mononuclear cells had been harvested by leukapheresis during the recovery phase following a course of progenitor-cell-mobilizing chemotherapy and G-CSF. Furthermore, a 91% pure peripheral CD34$^+$ hematopoietic progenitor cell suspension was prepared from the leukapheresis product of a patient (G.M.) suffering from plasmacytoma.

The number of peripheral CD34+progenitors was determined using a FACScan cytofluorometer. At least $10^5$ CD34+vital cells per sample were available for testing. In addition, nucleated blood cells of twenty patients with non-neoplastic disease were isolated using a red blood cell lysis-buffer (150 mM $NH_4Cl$, 10 mM $KHCO_3$, and 0.1 mM EDTA). The leukemia cell line K562 [ATCC CCL 243] served as the positive control in detection of wt1 mRNA and in immunofluorescence studies.

B. Indirect Immunofluorescence Assay

For the indirect immunofluorescence assay, mononuclear cells of bone marrow were isolated as already described. In addition, a 91% pure CD34+hematopoietic progenitor cell suspension was prepared from the leukapheresis product of a patient (G.M.) suffering from plasmacytoma. Prior to leukapheresis, she underwent peripheral stem-cell mobilization with chemotherapy (VAD-protocol) and G-CSF.

An aliquot taken from the leukapheresis product contained $2.5 \times 10^8$ mononuclear cells and, according to FACS analysis [M. Notter et al, Blood, 82:3113 (1993)], $8.75 \times 10^6$ CD34+hematopoietic progenitor cells. First, T-lymphocytes and myeloid cells were depleted using paramagnetic microbeads coupled with mouse anti-human CD3 and CD33 MAbs (Miltenyi, Cologne, Germany). Using a B2 column (Miltenyi), the cells were sorted according to the manufacturer's instructions. Subsequently, CD34+hematopoietic progenitor cells were isolated using the CD34 Progenitor Isolation Kit (QBEND/10) from Miltenyi. After removal of unbound MAb by washing, cells were passed twice over a Mini MACS column (without flow resistor, Miltenyi). The 8G12-PE MAb (Becton Dickinson, Heidelberg, Germany) was used to determine the purity of the final CD34+cell suspension, which was 91% with a yield of 39%.

One fraction of the cell preparations was processed according to the RT-PCR protocol described to detect the wt1 transcript. Another fraction was used in the immunofluorescence assay. K562 cells served as positive controls. For detection of the nuclear protein WT1, $5 \times 10^4$ mononuclear cells were cytocentrifuged onto glass slides and air-dried for 2 hours. To destroy cellular membranes, the cells were exposed to pure methanol for 30 minutes at 4° C. and then washed twice in PBS. The cells were incubated for 45 minutes at 4° C. with the mouse antihuman WT1 MAb H2, produced as described in Example 3 above, or a negative control MAb (MAb 425) recognizing the EGF-receptor [Rodeck et al, Cancer Res., 47:3692 (1987)]. The cells were washed again in PBS and incubated for 30 minutes with fluoresceinisothiocyanate (FITC)-conjugated goat anti-mouse F(ab')₂ fragments (Immunotech, Marseille, France). After washing in PBS, cells were embedded in PBS-glycerin and analyzed by fluorescence microscopy (Axiophot, 1000x, Zeiss, Oberkochem, Germany). Results are reported below in Table 1.

TABLE 1

| Patient Diagnosis | wt1 mRNA Initials | Nuclear Immunofluorescence Expression | MAb H2 | MAb 425 |
|---|---|---|---|---|
| ALL | | | | |
| pre-pre-B-ALL | C. R. | yes | #yes | $no |
| c-ALL | R. P. | yes | yes | no |
| c-ALL | F. G. | yes | yes | no |
| c-ALL | W. T. | no | no | no |
| T-ALL | A. D. | yes | no | no |
| T-ALL | M. S. | no | no | no |
| AML | | | | |
| AML-FAB-M2 | M. E. | yes | yes | no |
| AML-FAB-M4 | A. M. | yes | yes | no |
| AML-FAB-M2 | H. K. | yes | no | no |
| AML-FAB-M1 | H. L. | no | no | no |
| Controls | | | | |
| K562 cells | | yes | yes | no |
| CD34 + 91% pure progenitor cells | G. M. | no | no | no |
| normal blood mononuclear cells | | no | no | no | indicates more than 30% of cells show a strong nuclear fluorescence.
$ indicates no cells show nuclear fluorescence.

The indirect immunofluorescence assay with the MAb H2 directed against the WT1 nuclear protein disclosed a strong and specific nuclear fluorescence in blast cells from 3 of 6 ALL patients and 2 of 4 AML patients tested (Table 1). No nuclear immunofluorescence was observed in 3 ALL patients, one with (A.D.) and two without wt1 gene expression. In mononuclear cell preparations from 4 AML patients a nuclear immunofluorescence with MAb H2 was found in 2 cases and both tested positive for wt1 mRNA expression using RT-PCR. While blast cells of one AML patient did not express the Wt1 mRNA and had no nuclear immunofluorescence with MAb H2, those of another AML patient did show transcription of the wt1 mRNA but no nuclear immunofluorescence (H.K., Table 1). K562 cells showed strong nuclear immunofluorescence with MAb 6F-H2, whereas normal mononuclear blood cells and cells of a 91% pure CD34+hematopoietic progenitor cell suspension did not (Table 1). There was no nuclear immunofluorescence detectable using the negative control MAb 425 (Table 1). In normal blood granulocytes, cytoplasmic but no nuclear fluorescence was found with MAb H2 and regarded as unspecific (data not shown).

Immunofluorescence using MAb H2 confirms RT-PCR data, and shows detection of the WT1 protein in nuclei of leukemic blast cells but not in those of normal mononuclear cells or mononuclear cells enriched with CD34+ hematopoietic progenitors.

Expression of protein occurs following the transcription of mRNA message from the double stranded DNA. This mRNA is translated into a protein. Detectable mRNA indicates that the necessary "intermediate" is present and potentially capable of being translated into protein. However, this correlation does not always occur and the presence of mRNA does not necessarily mean the protein is being produced. Therefore, immunofluorescence detects protein expression and is the preferable assay system.

EXAMPLE 6—DETECTION OF WT1 PROTEIN IN MALIGNANT MESOTHELIOMAS

A. Cell Lines

The mesothelioma cell lines (ML1-ML19) used in the study were all developed from human mesothelioma tumors diagnosed using conventional immunohistochemical tests. Cell lines ML-10 and ML-16 were established by explant culture at the University of Pennsylvania [W. R. Smythe et al, Ann. Thorac. Surg., 57(6):1395–1401 (1994)]. Both cell lines have been passaged over 25 times without evidence of senescence, grow as tumors in immunodeficient mice, and show a staining pattern characteristic of mesothelioma with lack of staining with LeuM1 and carcinoembryonic antigen (CEA) antibodies. Cell lines ML1–ML8 were developed in the Surgical Oncology Laboratory at the National Cancer Institute (USA). Mesothelioma cell lines, (ML11–ML15) and lung cancer lines (LL5–LL8) were provided by Dr. Carmen Allegra from the Medical Oncology Branch, NCI-Navy, National Naval Medical Center. Cell lines: ML9 (H-Meso), ML17, ML18 and ML19 were provided by Dr. Joseph Testa from Fox Chase Cancer Institute, Philadelphia, Pa. Normal mesothelial cells were developed from explants derived from non-malignant visceral pleural tissue obtained at surgery.

These cell lines were maintained in RPMI-40 media (Gibco-BRL, Gaithersburg, Md.) supplemented with 10% fetal calf bovine serum, non-essential amino acids (10 mM), L-Glutamine (200 mM), penicillin (0.1 mg/ml) and streptomycin (0.1 mg/ml). The six lung cancer cell lines, LL1 (A549), LL2 (Calu-1), LL3 (Calu-3), LL4 (Calu-6), LL9 (SK-LU-1), LL10 (SK-MES1), were purchased from American Type Culture Collection (ATCC) and cultured per instructions. Normal bronchial epithelial cells [S. A. Mette et al, *Am. J. Respir. Cell. Mol. Biol.*, 8:562–572 (1993)] (HBE4) and human umbilical vein endothelial cells were cultured as described in S. M. Albelda et. al., *J. Clin. Invest.*, 83:1992–2002 (1989)].

B. Transfection Protocol

To generate a positive control for cellular localization studies of WT1 protein, COS-1 cells (ATCC) were either seeded at $5 \times 10^4$ cells/cm$^2$ onto 1% gelatin-coated coverslips or at $5 \times 10^5$ cells in a 35 mm dish and maintained in DMEM (Gibco-BRL, Gaithesburg, Md.) plus 10% fetal bovine serum. Twenty-four hours later, 2.5 µg of pCMVhuWT1cDNA, an expression vector described previously [Morris et al, cited above] was transfected into the cells by the calcium phosphate-mediated co-precipitation method [J. Sambrook et al, cited above]. Three days later the cells on the coverslips were processed for immunofluorescence staining with WT1 antibody and cells in 35 mm dish were harvested for immunoblot analysis which is described below.

C. Human Tissue and Tumor Specimens

Excess tissue specimens from normal organs, 9 mesothelioma tumors (Table 2), and 9 non-small cell lung carcinomas (NSCLC) were obtained freshly at the time of surgery and either immediately frozen in liquid nitrogen or frozen on dry ice after embedding in O.C.T. compound (Miles Scientific, Elkhart, Ind.). Samples were stored at −70° C. until further analysis. All diagnoses for the tumors were made by the pathologists at the University of Pennsylvania based on conventional histological and clinical criteria. Mesothelioma tumors were stained immunohistochemically and were characteristically negative for LeuM1 and CEA. Results are reported in Table 2 below.

TABLE 2

| Sample | Age | Sex | Histologic Type |
|---|---|---|---|
| MT1 | 56 | M | Epithelial malignant mesothelioma (MM) |
| MT2 | 69 | F | Epithelial MM |
| MT3 | 59 | F | Mixed MM |
| MT4 | 51 | M | Spindle Cell MM |
| MT5 | 61 | M | Mixed MM |
| MT6 | 72 | M | Fibrosarcomatous MM |
| MT7 | 70 | M | Inflammatory MM |

TABLE 2-continued

| Sample | Age | Sex | Histologic Type |
|---|---|---|---|
| MT8 | 65 | M | Epithelial MM |
| MT9 | — | 0 | Benign fibrous tumor |

D. Immunoblot Analysis

To determine if the WT1 protein was expressed in mesothelioma cell lines, immunoblotting experiments were performed, as follows, on nuclear extracts using the H2 anti-WT1 MAb prepared as described in Example 3 above.

Nuclear extracts were prepared from cell lines using standard techniques [F. M. Ausubel et al, *In Current Protocols in Molecular Biology*, John Wiley and Sons, New York (1991)]. The nuclear pellet was collected by centrifugation at 4000 rpm for 15 minutes at 4° C., resuspended in 5 times the pellet volume in electrophoresis sample buffer (62.5 mM Tris-HCl, 2% SDS, 10% glycerol, pH 6.8), and boiled for 5 minutes. Seventy-five µl of nuclear extract was applied on a 10% SDS-polyacrylamide gel under reducing conditions. The separated proteins were transferred to a nitrocellulose membrane which was developed as previously described [K. A. Knudsen et al, *Exp. Cell. Res.*, 157:218–226 (1985)] using anti-WT1 as a primary antibody and an alkaline phosphatase-coupled anti-mouse as the secondary antibody.

The H2 MAb recognized a 52 KDa protein from the COS-1 cells transfected with pCMVhuWT1cDNA. No WT1 expression was seen in non-transfected cells or in LL1, a lung cancer cell. However, in the ML17, ML13, ML16, and ML14 mesothelioma cell lines the antibody recognized two (52 and 55 KDa) proteins in varying amounts.

E. Immunolocalization Studies

1. Immunofluorescence

In order to determine the cellular location of the WT1 protein and to confirm the immunoblotting experiments, immunofluorescence staining was performed on some of the mesothelioma cell lines, as follows.

Cell lines ML13 and ML16 which express elevated levels of WT1 mRNA (determined using conventional RT-PCR techniques) were analyzed and LL1 used as a negative control, since it expressed almost no WT1 mRNA. An isotyped matched monoclonal antibody against the endothelial cell specific molecule, PECAM-1 was used as a non-reactive control. Confluent monolayers of cells grown on glass coverslips coated with 1% gelatin were processed as previously described [S. M. Albelda et al, cited above]. Immunofluorescence studies were performed with a 1:250 dilution of anti-WT1 ascites and a 1/200 fluorescein-conjugated anti-mouse antibody (Cappell Labs, Malvern, Pa.). The coverslips were evaluated under epifluorescence. COS-1 cells grown on coverslips and transfected with pCMVhuWT1cDNA, were used as a positive control.

COS-1 cells transfected with pCMVhuWT1cDNA stained strongly with the monoclonal anti-WT1 H2 with expression confined to the nucleus. In contrast, the untransfected COS-1 cells showed only baseline fluorescence. A similar nuclear staining pattern has been seen in COS-1 cells transfected with WT1cDNA and stained with a polyclonal anti-WT1 antibody [J. F. Tet al, cited above]. Clear nuclear staining with the anti-WT1 H2 MAb was also seen in the ML13 and the ML16 mesothelioma cell lines. In contrast, the lung cancer cell line (LL1) which did not express any WT1 mRNA did not stain positively with the anti-WT1 antibody. No appreciable staining was seen with the control antibody on any of the cell lines tested indicating the specificity of WT1 MAb.

2. Immunohistochemistry

In addition to evaluating WT1 protein expression in cell lines, the WT1 protein expression was evaluated in tissues by immunohistochemical staining. Frozen sections from 5 mesotheliomas and 5 NSCLC solid tumor specimens were stained with anti-WT1 MAb and a control MAb.

For immunohistochemistry, thin sections (5 μm) were prepared from frozen tissues embedded in O.C.T., fixed in acetone at −20° C. for 5 minutes and stored at −70° C. Prior to staining, the sections were blocked with 5% horse serum in PBS and washed twice in PBS at room temperature. The sections were incubated with a 1/1000 dilution of primary WT1 monoclonal antibody diluted in PBS/4% bovine serum albumin (BSA) for 1 hour at room temperature. Sections were washed twice in PBS/4% BSA, and then incubated for 30 minutes with a 1/1000 diluted biotinylated IgG horse antibody to mouse. The streptavidin-biotin ABC peroxidase detection system (Vector, Burlingame, Calif.) was applied, followed by a 2 minute incubation with 3-amino-9-ethylcarbazole (AEC) (Zymed, San Francisco, Calif.) as the substrate. The sections were mounted and evaluated microscopically.

Strong, primarily nuclear, staining was noted in a subset of identifiable neoplastic cells (5–10%) in all 5 mesothelioma tumors. Nuclear staining was not observed with a control MAb. Immunohistochemical staining of WT-1 was not observed, in any of the 5 non-small cell lung carcinomas examined as illustrated for LC4 and LC8.

F. Results

Immunohistochemical staining of both the mesothelioma tumors and the cell lines with the anti-WT1 monoclonal antibody, H2, further revealed that WT1 protein is expressed abundantly. As predicted for a transcription factor, the WT1 protein localized to the nucleus in a proportion of cells in culture and in tumors. Although the staining of WT1 protein has been observed in F9 embryonic carcinoma cells and in K562 cells [A. Telerman et al. Oncogene, 8:2545–2548 (1992)], immunohistochemical localization of WT1 in human tissues has not been previously reported. The general pattern of the expression WT1 protein was somewhat heterogeneous in mesothelioma tumors, however, WT1 was consistently expressed in at least some cells of all the tumors examined. Immunoblot analysis of nuclear extracts from mesothelioma cell lines revealed the presence of a 52 KDa and a 54 KDa sized WT1 proteins. Whether the two proteins represent alternatively spliced WT1 iso-forms [D. A. Haber et al. Proc. Natl. Acad. Sci. USA, 88:9618–9622 (1991)] or a single form differently processed in the cancer cells is not known.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

---

What is claimed is:

1. A method for diagnosing a disease condition characterized by WT1 expression comprising the steps of:
    a) providing a biological sample from a patient having the clinical symptoms associated with mesothelioma;
    b) providing a monoclonal antibody selected from the group consisting of H2 which is secreted by hybridoma cell line ATCC No. 11598, H7 which is secreted by hybridoma cell line ATCC No. 11599, HC17 which is secreted by hybridoma cell line ATCC No. 11600, and a cocktail of any combination of the H2, H7 and HC17 antibodies;
    c) contacting said sample with said monoclonal antibody; and
    d) detecting the presence of binding of said monoclonal antibody to said biological sample, wherein the presence of such binding indicates the presence of said disease condition.

2. The method according to claim 1, wherein said biological sample is selected from the group consisting of whole blood, serum, plasma, synovial fluid, and tissue and said disease condition is selected from the group consisting of mesothelioma, prostate cancer, ovarian cancer, and leukemia.

3. A method of monitoring therapy in leukemia patients comprising the steps of:
    a) providing a biological sample from a patient treated for leukemia;
    b) providing a monoclonal antibody selected from the group consisting of H2 which is secreted by hybridoma cell line ATCC No. 11598, H7 which is secreted bY hybridoma cell line ATCC No. 11599, HC17 which is secreted by hybridoma cell line ATCC No. 11600, and a cocktail of any combination of the H2, H7 and HC17 antibodies;
    c) contacting said sample with said monoclonal antibody; and
    d) detecting the presence of binding of said monoclonal antibody to said biological sample, wherein the presence of such binding indicates the presence of active leukemia cells.

4. The method according to claim 3, wherein said biological sample is selected from the group consisting of whole blood, plasma, serum, urine and bone marrow.

\* \* \* \* \*

UNITED STATES PATENT AND TRADEMARK OFFICE
CERTIFICATE OF CORRECTION

PATENT NO. : 5,633,142

DATED : May 27, 1997

INVENTOR(S) : Meenhard Herlyn, Jennifer Morris, Frank J. Rauscher, III, and Ulrich Rodeck It is certified that error appears in the above-indentified patent and that said Letters Patent is hereby corrected as shown below:

Col. 2, line 4, before "2545-2548", insert -- 7: --.

Col. 2, line 42, before "11598", insert -- HB- --.

Col. 2, line 44, before "11599", insert -- HB- --.

Col. 2, line 45, before "11600", insert -- HB- --.

Col. 6, line 10, before "11598", insert -- HB- --.

Col. 6, line 11, before "11599", insert -- HB- --.

Col. 6, line 12, before "11600", insert -- HB- --.

Col. 9, line 35, delete "Ico" and insert in place thereof -- Nco --.

Col. 15, line 21, delete "(SK-MES1)" and insert in place thereof -- (SK-MES-1) --.

Col. 28, Claim 3, line 50, delete "bY" and insert in place thereof -- by --.

Col. 27, Claim 1, line 50, before "11598", insert -- HB- --.

Col. 27, Claim 1, line 51, before "11599", insert -- HB- --.

Col. 27, Claim 1, line 52, before "11600", insert -- HB- --.

Col. 28, Claim 3, line 50, before "11598", insert -- HB- --.

UNITED STATES PATENT AND TRADEMARK OFFICE
CERTIFICATE OF CORRECTION

PATENT NO. : 5,633,142
DATED : May 27, 1997
INVENTOR(S) : Herlyn, et al

It is certified that error appears in the above-indentified patent and that said Letters Patent is hereby corrected as shown below:

Col. 28, Claim 3, line 51, before "11599", insert -- HB- --.

Col. 28, Claim 3, line 52, before "11600", insert -- HB- --.

Signed and Sealed this

Sixteenth Day of September, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 633 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..630

( x i ) SEQUENCE DESCRIPTION: SEQ ID NO:1:

```
ATG AGA GGA TCG CAT CAC CAT CAC CAT CAC TCC ATG GGT TCC GAC GTT      48
Met Arg Gly Ser His His His His His His Ser Met Gly Ser Asp Val
 1               5                  10                  15

CGT GAC CTG AAC GCA CTG CTG CCG GCA GTT CCG TCC CTG GGT GGT GGT      96
Arg Asp Leu Asn Ala Leu Leu Pro Ala Val Pro Ser Leu Gly Gly Gly
                20                  25                  30

GGT GGT TGC GCA CTG CCG GTT AGC GGT GCA GCA CAG TGG GCT CCG GTT     144
Gly Gly Cys Ala Leu Pro Val Ser Gly Ala Ala Gln Trp Ala Pro Val
        35                  40                  45

CTG GAC TTC GCA CCG CCG GGT GCA TCC GCA TAC GGT TCC CTG GGT GGT     192
Leu Asp Phe Ala Pro Pro Gly Ala Ser Ala Tyr Gly Ser Leu Gly Gly
        50                  55                  60

CCG GCA CCG CCG CCG GCA CCG CCG CCG CCG CCG CCG CCG CCG CCG CAC     240
Pro Ala Pro Pro Pro Ala Pro Pro Pro Pro Pro Pro Pro Pro Pro His
65                  70                  75                  80

TCC TTC ATC AAA CAG GAA CCG AGC TGG GGT GGT GCA GAA CCG CAC GAA     288
Ser Phe Ile Lys Gln Glu Pro Ser Trp Gly Gly Ala Glu Pro His Glu
                85                  90                  95
```

-continued

| | | | | | | | | | | | | | | | | |
|---|---|---|---|---|---|---|---|---|---|---|---|---|---|---|---|---|
| GAA | CAG | TGC | CTG | AGC | GCA | TTC | ACC | GTT | CAC | TTC | TCC | GGC | CAG | TTC | ACT | 336 |
| Glu | Gln | Cys | Leu | Ser | Ala | Phe | Thr | Val | His | Phe | Ser | Gly | Gln | Phe | Thr | |
| | | | 100 | | | | | 105 | | | | | 110 | | | |
| GGC | ACA | GCC | GGA | GCC | TGT | CGC | TAC | GGG | CCC | TTC | GGT | CCT | CCT | CCG | CCC | 384 |
| Gly | Thr | Ala | Gly | Ala | Cys | Arg | Tyr | Gly | Pro | Phe | Gly | Pro | Pro | Pro | Pro | |
| | | 115 | | | | | 120 | | | | | 125 | | | | |
| AGC | CAG | GCG | TCA | TCC | GGC | CAG | GCC | AGG | ATG | TTT | CCT | AAC | GCG | CCC | TAC | 432 |
| Ser | Gln | Ala | Ser | Ser | Gly | Gln | Ala | Arg | Met | Phe | Pro | Asn | Ala | Pro | Tyr | |
| | 130 | | | | | 135 | | | | | 140 | | | | | |
| CTG | CCC | AGC | TGC | CTC | GAG | AGC | CAG | CCC | GCT | ATT | CGC | AAT | CAG | GGT | TAC | 480 |
| Leu | Pro | Ser | Cys | Leu | Glu | Ser | Gln | Pro | Ala | Ile | Arg | Asn | Gln | Gly | Tyr | |
| 145 | | | | | 150 | | | | | 155 | | | | | 160 | |
| AGC | ACG | GTC | ACC | TTC | GAC | GGG | ACG | CCC | AGC | TAC | GGT | CAC | ACG | CCC | TCG | 528 |
| Ser | Thr | Val | Thr | Phe | Asp | Gly | Thr | Pro | Ser | Tyr | Gly | His | Thr | Pro | Ser | |
| | | | | 165 | | | | | 170 | | | | | 175 | | |
| CAC | CAT | GCG | GCG | CAG | TTC | CCC | AAC | CAC | TCA | TTC | AAG | CAT | GAG | GAT | CCG | 576 |
| His | His | Ala | Ala | Gln | Phe | Pro | Asn | His | Ser | Phe | Lys | His | Glu | Asp | Pro | |
| | | | 180 | | | | | 185 | | | | | 190 | | | |
| GCT | GCT | AAC | AAA | GCC | CGA | AAG | GAA | GCT | GAG | TTG | GCT | GCT | GCC | ACC | GCT | 624 |
| Ala | Ala | Asn | Lys | Ala | Arg | Lys | Glu | Ala | Glu | Leu | Ala | Ala | Ala | Thr | Ala | |
| | | 195 | | | | | 200 | | | | | 205 | | | | |
| GAG | CAA | TAA | | | | | | | | | | | | | | 633 |
| Glu | Gln | | | | | | | | | | | | | | | |
| 210 | | | | | | | | | | | | | | | | |

( 2 ) INFORMATION FOR SEQ ID NO:2:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Arg | Gly | Ser | His | His | His | His | His | His | Ser | Met | Gly | Ser | Asp | Val |
| 1 | | | | 5 | | | | | 10 | | | | | 15 | |
| Arg | Asp | Leu | Asn | Ala | Leu | Leu | Pro | Ala | Val | Pro | Ser | Leu | Gly | Gly | Gly |
| | | | | 20 | | | | | 25 | | | | | 30 | |
| Gly | Gly | Cys | Ala | Leu | Pro | Val | Ser | Gly | Ala | Ala | Gln | Trp | Ala | Pro | Val |
| | | | 35 | | | | | 40 | | | | | 45 | | |
| Leu | Asp | Phe | Ala | Pro | Pro | Gly | Ala | Ser | Ala | Tyr | Gly | Ser | Leu | Gly | Gly |
| | | 50 | | | | | 55 | | | | | 60 | | | |
| Pro | Ala | Pro | Pro | Pro | Ala | Pro | Pro | Pro | Pro | Pro | Pro | Pro | Pro | Pro | His |
| 65 | | | | | 70 | | | | | 75 | | | | | 80 |
| Ser | Phe | Ile | Lys | Gln | Glu | Pro | Ser | Trp | Gly | Gly | Ala | Glu | Pro | His | Glu |
| | | | | 85 | | | | | 90 | | | | | 95 | |
| Glu | Gln | Cys | Leu | Ser | Ala | Phe | Thr | Val | His | Phe | Ser | Gly | Gln | Phe | Thr |
| | | | | 100 | | | | | 105 | | | | | 110 | |
| Gly | Thr | Ala | Gly | Ala | Cys | Arg | Tyr | Gly | Pro | Phe | Gly | Pro | Pro | Pro | Pro |
| | | | 115 | | | | | 120 | | | | | 125 | | |
| Ser | Gln | Ala | Ser | Ser | Gly | Gln | Ala | Arg | Met | Phe | Pro | Asn | Ala | Pro | Tyr |
| | | 130 | | | | | 135 | | | | | 140 | | | |
| Leu | Pro | Ser | Cys | Leu | Glu | Ser | Gln | Pro | Ala | Ile | Arg | Asn | Gln | Gly | Tyr |
| 145 | | | | | 150 | | | | | 155 | | | | | 160 |
| Ser | Thr | Val | Thr | Phe | Asp | Gly | Thr | Pro | Ser | Tyr | Gly | His | Thr | Pro | Ser |
| | | | | 165 | | | | | 170 | | | | | 175 | |
| His | His | Ala | Ala | Gln | Phe | Pro | Asn | His | Ser | Phe | Lys | His | Glu | Asp | Pro |
| | | | 180 | | | | | 185 | | | | | 190 | | |

```
Ala  Ala  Asn  Lys  Ala  Arg  Lys  Glu  Ala  Glu  Leu  Ala  Ala  Ala  Thr  Ala
          195                      200                      205

Glu  Gln
     210
```

( 2 ) INFORMATION FOR SEQ ID NO:3:

( i ) SEQUENCE CHARACTERISTICS:
        ( A ) LENGTH: 1680 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 381..1670

( x i ) SEQUENCE DESCRIPTION: SEQ ID NO:3:

```
GTTCAAGGCA  GCGCCCACAC  CCGGGGGCTC  TGCGCAACCC  GACCGCCTGT  CCGCTCCCCC    60

ACTTCCCGCC  CTCCCTCCCA  CCTACTCATT  CACCCACCCA  CCCACCCAGA  GCCGGGACGG   120

CAGCCCAGGC  GCCCGGGCCC  CGCCGTCTCC  TCGCCGCGAT  CCTGGACTTC  CTCTTGCTGC   180

AGGACCCGGC  TTCCACGTGT  GTCCCGGAGC  CGGCGTCTCA  GCACACGCTC  CGCTCCGGGC   240

CTGGGTGCCT  ACAGCAGCCA  GAGCAGCAGG  GAGTCCGGGA  CCCGGGCGGC  ATCTGGGCCA   300

AGTTAGGCGC  CGCCGAGGCC  AGCGCTGAAC  GTCTCCAGGG  CCGGAGGAGC  CGCGGGGCGT   360

CCGGGTCTGA  GCCTCAGCAA  ATG  GGC  TCC  GAC  GTG  CGG  GAC  CTG  AAC  GCG   410
                           Met  Gly  Ser  Asp  Val  Arg  Asp  Leu  Asn  Ala
                             1                5                         10

CTG  CTG  CCC  GCC  GTC  CCC  TCC  CTG  GGT  GGC  GGC  GGC  TGT  GCC  CTG   458
Leu  Leu  Pro  Ala  Val  Pro  Ser  Leu  Gly  Gly  Gly  Gly  Cys  Ala  Leu
              15                       20                       25

CCT  GTG  AGC  GGC  GCG  GCG  CAG  TGG  GCG  CCG  GTG  CTG  GAC  TTT  GCG  CCC   506
Pro  Val  Ser  Gly  Ala  Ala  Gln  Trp  Ala  Pro  Val  Leu  Asp  Phe  Ala  Pro
                    30                       35                       40

CCG  GGC  GCT  TCG  GCT  TAC  GGG  TCG  TTG  GGC  GGC  CCC  GCG  CCG  CCA  CCG   554
Pro  Gly  Ala  Ser  Ala  Tyr  Gly  Ser  Leu  Gly  Gly  Pro  Ala  Pro  Pro  Pro
               45                       50                       55

GCT  CCG  CCG  CCA  CCC  CCG  CCG  CCG  CCT  CAC  TCC  TTC  ATC  AAA  CAG   602
Ala  Pro  Pro  Pro  Pro  Pro  Pro  Pro  Pro  His  Ser  Phe  Ile  Lys  Gln
     60                       65                       70

GAG  CCG  AGC  TGG  GGC  GGC  GCG  GAG  CCG  CAC  GAG  GAG  CAG  TGC  CTG  AGC   650
Glu  Pro  Ser  Trp  Gly  Gly  Ala  Glu  Pro  His  Glu  Glu  Gln  Cys  Leu  Ser
75                       80                       85                       90

GCC  TTC  ACT  GTC  CAC  TTT  TCC  GGC  CAG  TTC  ACT  GGC  ACA  GCC  GGA  GCC   698
Ala  Phe  Thr  Val  His  Phe  Ser  Gly  Gln  Phe  Thr  Gly  Thr  Ala  Gly  Ala
                    95                      100                      105

TGT  CGC  TAC  GGG  CCC  TTC  GGT  CCT  CCT  CCG  CCC  AGC  CAG  GCG  TCA  TCC   746
Cys  Arg  Tyr  Gly  Pro  Phe  Gly  Pro  Pro  Pro  Pro  Ser  Gln  Ala  Ser  Ser
               110                      115                      120

GGC  CAG  GCC  AGG  ATG  TTT  CCT  AAC  GCG  CCC  TAC  CTG  CCC  AGC  TGC  CTC   794
Gly  Gln  Ala  Arg  Met  Phe  Pro  Asn  Ala  Pro  Tyr  Leu  Pro  Ser  Cys  Leu
          125                      130                      135

GAG  AGC  CAG  CCC  GCT  ATT  CGC  AAT  CAG  GGT  TAC  AGC  ACG  GTC  ACC  TTC   842
Glu  Ser  Gln  Pro  Ala  Ile  Arg  Asn  Gln  Gly  Tyr  Ser  Thr  Val  Thr  Phe
     140                      145                      150

GAC  GGG  ACG  CCC  AGC  TAC  GGT  CAC  ACG  CCC  TCG  CAC  CAT  GCG  GCG  CAG   890
Asp  Gly  Thr  Pro  Ser  Tyr  Gly  His  Thr  Pro  Ser  His  His  Ala  Ala  Gln
155                      160                      165                      170
```

-continued

| | | | | | | | | | | | | | | | | |
|---|---|---|---|---|---|---|---|---|---|---|---|---|---|---|---|---|
| TTC | CCC | AAC | CAC | TCA | TTC | AAG | CAT | GAG | GAT | CCC | ATG | GGC | CAG | CAG | GGC | 938 |
| Phe | Pro | Asn | His | Ser | Phe | Lys | His | Glu | Asp | Pro | Met | Gly | Gln | Gln | Gly | |
| | | | | 175 | | | | | 180 | | | | | 185 | | |
| TCG | CTG | GGT | GAG | CAG | CAG | TAC | TCG | GTG | CCG | CCC | CCG | GTC | TAT | GGC | TGC | 986 |
| Ser | Leu | Gly | Glu | Gln | Gln | Tyr | Ser | Val | Pro | Pro | Pro | Val | Tyr | Gly | Cys | |
| | | | 190 | | | | | 195 | | | | | 200 | | | |
| CAC | ACC | CCC | ACC | GAC | AGC | TGC | ACC | GGC | AGC | CAG | GCT | TTG | CTG | CTG | AGG | 1034 |
| His | Thr | Pro | Thr | Asp | Ser | Cys | Thr | Gly | Ser | Gln | Ala | Leu | Leu | Leu | Arg | |
| | | 205 | | | | | 210 | | | | | 215 | | | | |
| ACG | CCC | TAC | AGC | AGT | GAC | AAT | TTA | TAC | CAA | ATG | ACA | TCC | CAG | CTT | GAA | 1082 |
| Thr | Pro | Tyr | Ser | Ser | Asp | Asn | Leu | Tyr | Gln | Met | Thr | Ser | Gln | Leu | Glu | |
| | 220 | | | | | 225 | | | | | 230 | | | | | |
| TGC | ATG | ACC | TGG | AAT | CAG | ATG | AAC | TTA | GGA | GCC | ACC | TTA | AAG | GGA | CAC | 1130 |
| Cys | Met | Thr | Trp | Asn | Gln | Met | Asn | Leu | Gly | Ala | Thr | Leu | Lys | Gly | His | |
| 235 | | | | | 240 | | | | | 245 | | | | | 250 | |
| AGC | ACA | GGG | TAC | GAG | AGC | GAT | AAC | CAC | ACA | ACG | CCC | ATC | CTC | TGC | GGA | 1178 |
| Ser | Thr | Gly | Tyr | Glu | Ser | Asp | Asn | His | Thr | Thr | Pro | Ile | Leu | Cys | Gly | |
| | | | | 255 | | | | | 260 | | | | | 265 | | |
| GCC | CAA | TAC | AGA | ATA | CAC | ACG | CAC | GGT | GTC | TTC | AGA | GGC | ATT | CAG | GAT | 1226 |
| Ala | Gln | Tyr | Arg | Ile | His | Thr | His | Gly | Val | Phe | Arg | Gly | Ile | Gln | Asp | |
| | | | 270 | | | | | 275 | | | | | 280 | | | |
| GTG | CGA | CGT | GTG | CCT | GGA | GTA | GCC | CCG | ACT | CTT | GTA | CGG | TCG | GCA | TCT | 1274 |
| Val | Arg | Arg | Val | Pro | Gly | Val | Ala | Pro | Thr | Leu | Val | Arg | Ser | Ala | Ser | |
| | | 285 | | | | | 290 | | | | | 295 | | | | |
| GAG | ACC | AGT | GAG | AAA | CGC | CCC | TTC | ATG | TGT | GCT | TAC | CCA | GGC | TGC | AAT | 1322 |
| Glu | Thr | Ser | Glu | Lys | Arg | Pro | Phe | Met | Cys | Ala | Tyr | Pro | Gly | Cys | Asn | |
| | 300 | | | | | 305 | | | | | 310 | | | | | |
| AAG | AGA | TAT | TTT | AAG | CTG | TCC | CAC | TTA | CAG | ATG | CAC | AGC | AGG | AAG | CAC | 1370 |
| Lys | Arg | Tyr | Phe | Lys | Leu | Ser | His | Leu | Gln | Met | His | Ser | Arg | Lys | His | |
| 315 | | | | | 320 | | | | | 325 | | | | | 330 | |
| ACT | GGT | GAG | AAA | CCA | TAC | CAG | TGT | GAC | TTC | AAG | GAC | TGT | GAA | CGA | AGG | 1418 |
| Thr | Gly | Glu | Lys | Pro | Tyr | Gln | Cys | Asp | Phe | Lys | Asp | Cys | Glu | Arg | Arg | |
| | | | | 335 | | | | | 340 | | | | | 345 | | |
| TTT | TCT | CGT | TCA | GAC | CAG | CTC | AAA | AGA | CAC | CAA | AGG | AGA | CAT | ACA | GGT | 1466 |
| Phe | Ser | Arg | Ser | Asp | Gln | Leu | Lys | Arg | His | Gln | Arg | Arg | His | Thr | Gly | |
| | | | 350 | | | | | 355 | | | | | 360 | | | |
| GTG | AAA | CCA | TTC | CAG | TGT | AAA | ACT | TGT | CAG | CGA | AAG | TTC | TCC | CGG | TCC | 1514 |
| Val | Lys | Pro | Phe | Gln | Cys | Lys | Thr | Cys | Gln | Arg | Lys | Phe | Ser | Arg | Ser | |
| | | 365 | | | | | 370 | | | | | 375 | | | | |
| GAC | CAC | CTG | AAG | ACC | CAC | ACC | AGG | ACT | CAT | ACA | GGT | GAA | AAG | CCC | TTC | 1562 |
| Asp | His | Leu | Lys | Thr | His | Thr | Arg | Thr | His | Thr | Gly | Glu | Lys | Pro | Phe | |
| | 380 | | | | | 385 | | | | | 390 | | | | | |
| AGC | TGT | CGG | TGG | CCA | AGT | TGT | CAG | AAA | AAG | TTT | GCC | CGG | TCA | GAT | GAA | 1610 |
| Ser | Cys | Arg | Trp | Pro | Ser | Cys | Gln | Lys | Lys | Phe | Ala | Arg | Ser | Asp | Glu | |
| 395 | | | | | 400 | | | | | 405 | | | | | 410 | |
| TTA | GTC | CGC | CAT | CAC | AAC | ATG | CAT | CAG | AGA | AAC | ATG | ACC | AAA | CTC | CAG | 1658 |
| Leu | Val | Arg | His | His | Asn | Met | His | Gln | Arg | Asn | Met | Thr | Lys | Leu | Gln | |
| | | | | 415 | | | | | 420 | | | | | 425 | | |
| CTG | GCG | CTT | TGAGGGGTCT CCC | | | | | | | | | | | | | 1680 |
| Leu | Ala | Leu | | | | | | | | | | | | | | |
| | | 430 | | | | | | | | | | | | | | |

( 2 ) INFORMATION FOR SEQ ID NO:4:

( i ) SEQUENCE CHARACTERISTICS:
        ( A ) LENGTH: 429 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

-continued

| Met | Gly | Ser | Asp | Val | Arg | Asp | Leu | Asn | Ala | Leu | Leu | Pro | Ala | Val | Pro |
|---|---|---|---|---|---|---|---|---|---|---|---|---|---|---|---|
| 1 | | | | 5 | | | | | 10 | | | | | 15 | |
| Ser | Leu | Gly | Gly | Gly | Gly | Gly | Cys | Ala | Leu | Pro | Val | Ser | Gly | Ala | Ala |
| | | | 20 | | | | 25 | | | | | | 30 | | |
| Gln | Trp | Ala | Pro | Val | Leu | Asp | Phe | Ala | Pro | Pro | Gly | Ala | Ser | Ala | Tyr |
| | | 35 | | | | | 40 | | | | | | 45 | | |
| Gly | Ser | Leu | Gly | Gly | Pro | Ala | Pro | Pro | Ala | Pro | Pro | Pro | Pro |
| | 50 | | | | 55 | | | | | 60 | | | |
| Pro | Pro | Pro | Pro | His | Ser | Phe | Ile | Lys | Gln | Glu | Pro | Ser | Trp | Gly | Gly |
| 65 | | | | | 70 | | | | | 75 | | | | | 80 |
| Ala | Glu | Pro | His | Glu | Glu | Gln | Cys | Leu | Ser | Ala | Phe | Thr | Val | His | Phe |
| | | | | 85 | | | | | 90 | | | | | 95 | |
| Ser | Gly | Gln | Phe | Thr | Gly | Thr | Ala | Gly | Ala | Cys | Arg | Tyr | Gly | Pro | Phe |
| | | | 100 | | | | 105 | | | | | | 110 | | |
| Gly | Pro | Pro | Pro | Pro | Ser | Gln | Ala | Ser | Ser | Gly | Gln | Ala | Arg | Met | Phe |
| | | 115 | | | | | 120 | | | | | | 125 | | |
| Pro | Asn | Ala | Pro | Tyr | Leu | Pro | Ser | Cys | Leu | Glu | Ser | Gln | Pro | Ala | Ile |
| | 130 | | | | 135 | | | | | 140 | | | | | |
| Arg | Asn | Gln | Gly | Tyr | Ser | Thr | Val | Thr | Phe | Asp | Gly | Thr | Pro | Ser | Tyr |
| 145 | | | | | 150 | | | | | 155 | | | | | 160 |
| Gly | His | Thr | Pro | Ser | His | His | Ala | Ala | Gln | Phe | Pro | Asn | His | Ser | Phe |
| | | | | 165 | | | | | 170 | | | | | 175 | |
| Lys | His | Glu | Asp | Pro | Met | Gly | Gln | Gln | Gly | Ser | Leu | Gly | Glu | Gln | Gln |
| | | | 180 | | | | | 185 | | | | | 190 | | |
| Tyr | Ser | Val | Pro | Pro | Pro | Val | Tyr | Gly | Cys | His | Thr | Pro | Thr | Asp | Ser |
| | | | 195 | | | | 200 | | | | | | 205 | | |
| Cys | Thr | Gly | Ser | Gln | Ala | Leu | Leu | Leu | Arg | Thr | Pro | Tyr | Ser | Ser | Asp |
| | | 210 | | | | | 215 | | | | | 220 | | | |
| Asn | Leu | Tyr | Gln | Met | Thr | Ser | Gln | Leu | Glu | Cys | Met | Thr | Trp | Asn | Gln |
| 225 | | | | | 230 | | | | | 235 | | | | | 240 |
| Met | Asn | Leu | Gly | Ala | Thr | Leu | Lys | Gly | His | Ser | Thr | Gly | Tyr | Glu | Ser |
| | | | | 245 | | | | | 250 | | | | | 255 | |
| Asp | Asn | His | Thr | Thr | Pro | Ile | Leu | Cys | Gly | Ala | Gln | Tyr | Arg | Ile | His |
| | | | 260 | | | | | 265 | | | | | 270 | | |
| Thr | His | Gly | Val | Phe | Arg | Gly | Ile | Gln | Asp | Val | Arg | Arg | Val | Pro | Gly |
| | | | 275 | | | | 280 | | | | | 285 | | | |
| Val | Ala | Pro | Thr | Leu | Val | Arg | Ser | Ala | Ser | Glu | Thr | Ser | Glu | Lys | Arg |
| | | 290 | | | | 295 | | | | | 300 | | | | |
| Pro | Phe | Met | Cys | Ala | Tyr | Pro | Gly | Cys | Asn | Lys | Arg | Tyr | Phe | Lys | Leu |
| 305 | | | | | 310 | | | | | 315 | | | | | 320 |
| Ser | His | Leu | Gln | Met | His | Ser | Arg | Lys | His | Thr | Gly | Glu | Lys | Pro | Tyr |
| | | | | 325 | | | | | 330 | | | | | 335 | |
| Gln | Cys | Asp | Phe | Lys | Asp | Cys | Glu | Arg | Arg | Phe | Ser | Arg | Ser | Asp | Gln |
| | | | 340 | | | | | 345 | | | | | 350 | | |
| Leu | Lys | Arg | His | Gln | Arg | Arg | His | Thr | Gly | Val | Lys | Pro | Phe | Gln | Cys |
| | | 355 | | | | | 360 | | | | | 365 | | | |
| Lys | Thr | Cys | Gln | Arg | Lys | Phe | Ser | Arg | Ser | Asp | His | Leu | Lys | Thr | His |
| | | 370 | | | | | 375 | | | | | 380 | | | |
| Thr | Arg | Thr | His | Thr | Gly | Glu | Lys | Pro | Phe | Ser | Cys | Arg | Trp | Pro | Ser |
| 385 | | | | | 390 | | | | | 395 | | | | | 400 |
| Cys | Gln | Lys | Lys | Phe | Ala | Arg | Ser | Asp | Glu | Leu | Val | Arg | His | His | Asn |
| | | | | 405 | | | | | 410 | | | | | 415 | |
| Met | His | Gln | Arg | Asn | Met | Thr | Lys | Leu | Gln | Leu | Ala | Leu |
| | | | 420 | | | | | 425 | | | | | |

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:5:

CATGAGAGGA TCGCATCACC ATCACCATCA CTC    33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:6:

CATGGAGTGA TGGTGATGGT GATGCGATCC TCT    33

(2) INFORMATION FOR SEQ ID NO:7:

(i) SEQUENCE CHARACTERISTICS:
        (A) LENGTH: 17 amino acids
        (B) TYPE: amino acid
        (D) TOPOLOGY: unknown (ii) MOLECULE TYPE: protein (xi) SEQUENCE DESCRIPTION: SEQ ID NO:7:

Val Ala Ala Gly Ser Ser Ser Ser Val Lys Trp Thr Glu Gly Gln Ser
1               5                   10                  15
Asn